US006927192B2

(12) United States Patent
Martinelli et al.

(10) Patent No.: US 6,927,192 B2
(45) Date of Patent: Aug. 9, 2005

(54) PROCESS TO IMPROVE THE QUALITY OF GRAINS AND SEEDS

(75) Inventors: Jose A. Martinelli, Porto Alegre (BR); Marcia Martinelli, Porto Alegre (BR); R. Gary Fulcher, Arden Hills, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 58 days.

(21) Appl. No.: 10/367,604

(22) Filed: Feb. 13, 2003

(65) Prior Publication Data

US 2003/0180385 A1 Sep. 25, 2003

Related U.S. Application Data

(60) Provisional application No. 60/357,507, filed on Feb. 15, 2002.

(51) Int. Cl.[7] .............................................. A01N 25/26
(52) U.S. Cl. ...................................... 504/100; 424/661
(58) Field of Search ........................... 504/100; 424/661

(56) References Cited

U.S. PATENT DOCUMENTS

| | | | |
|---|---|---|---|
| 1,987,304 A | | 1/1935 | Menke |
| 3,203,810 A | | 8/1965 | Carey |
| 4,180,569 A | | 12/1979 | Goddard |
| 4,328,200 A | | 5/1982 | Welch et al. |
| 4,806,263 A | | 2/1989 | Leathers et al. |
| 5,968,830 A | * | 10/1999 | Dan et al. .................. 435/469 |

FOREIGN PATENT DOCUMENTS

| | | |
|---|---|---|
| BR | 9905040 | 11/2000 |
| CN | 1262279 | 8/2000 |
| EP | 067 479 | * 12/1982 |
| FR | 793628 | 1/1936 |
| JP | 56-021550 | 2/1981 |
| JP | 01306692 | 12/1989 |
| JP | 04008286 | 1/1992 |
| JP | 06070701 | 3/1994 |
| JP | 07179312 | 7/1995 |
| JP | 07214052 | 8/1995 |
| JP | 07313149 | * 12/1995 |
| JP | 2000313606 | 11/2000 |
| NL | 0240927 | 7/1959 |
| PL | 172955 | 12/1997 |
| WO | WO-9616555 | 6/1996 |
| WO | WO-2001067878 | 9/2001 |

OTHER PUBLICATIONS

Sauer et al, Disinfection of seed surfaces with sodium hypochlorite, Phytopathology, 1986, vol. 76 no. 7, pp. 745–749.*

Drew et al, The effects of pH during treatment of lettuce seeds with chlorine-releasing compounds on germination and seedling development, Annals of Applied Biology, 1985, vol. 106 no. 1, pp. 157–161.*

Abbey, A, et al., "Antibiotic inactivation in microbiological assay extracts of animal feed by sodium hypochlorite solution and heat", *J. Assoc. Offic. Agr. Chemists, 48*, Abstract Only,(1965),48.

Abdel–Aal, et al., "Bleaching of wheat distillers' grains and its fiber and protein fractions with alkaline hydrogen peroxide", *Food Sci. Technol. 29*, Abstract only,(1996), 210–216.

Abdul–Bai, A A., "Hypochlorite and tissue sterilization", *Planta, 115*, Abstract Only,(1974),373–376.

Abdul–Baki, A, et al., "Seed disinfection with hypochlorites: A selected literature review of hypochlorite chemistry and definition of terms", *J. Seed Technol., 4*, Abstract Only,(1979),43–56.

(Continued)

Primary Examiner—Alton Pryor
(74) Attorney, Agent, or Firm—Fish & Richardson P.C., P.A.

(57) ABSTRACT

The present invention provides a method of treating a grain or seed to reduce the contamination level of a seed-associated pathogen.

34 Claims, 9 Drawing Sheets

OTHER PUBLICATIONS

Adetuyi, F C., et al., "Antagonistic microflora from dried maize seed and their effect on seed germination", *Indian Journal of Mycology and Plant Pathology, 23*. Abstract Only,(1993),157–161.

Agbeniyi, S O., et al., "Effect of curing and pre–storage dip treatments on the control of storage mold of kola nuts", *Z. Lebensm.–Unters. Forsch. A. 208(1)*, Abstract only,(1999), 47–49.

Akpa, A D., et al., "Seed treatment chemicals in relation to sesame bacterial blight control", *Acta Phytopathol. Entomol. Hung., 28*, Abstract Only,(1993),123–127.

Aveling, T A., et al., "Evaluation of seed treatments for reducing *Alternaria porri* and *Stemphylium vesicarium* on onion seed", *Plant Dis., 77*, Abstract Only,(1993), 1009–1011.

Barbetti, M J., "Seed treatments for control of subterranean clover root rot", *Australasian Plant Pathology, 13*, Abstract Only,(1984),43–45.

Bol, J, et al., "Influence of microbial activity during malting on malt quality", *Hoofdgroep Voeding Voedingsmiddelen*, Abstract only,(1986).

Burrows, E P., et al.,"Chemical transformations of trichothecenes. Nuclear magnetic resonance (NMR) spectroscopic and mass spectrometric characterization of transformation products of verrucarol", *Gov. Rep. Announce, 87*, Abstract only,(1987),31.

Burrows, E, et al., "Hypochlorite–promoted transformations of trichothecenes, 3. Deoxynivalenol", *J. Nat. Prod., 50*, Abstract only,(1987),1108–1112.

Castegnaro, M, et al., "Problems related to the use of sodium hypochlorite in the detoxification of aflatoxin B1", *Am. Ind. Hyg. Assoc. J., 42*, Abstract only,(1981),398–401.

Cezard, R, "Orobanchaceae. II. Breaking dormancy in oroganchaceous seeds by removing an endogenous inhibition", *Bull. Acad. Soc. Lorraine Sci., 12*, Abstract Only,(1973), 97–120.

Chelkowski, J, et al., "Evaluation of the effectiveness of selected disinfectants on barley grain fungal spores", *Przem. Ferment. Owocowo–Warzywny, 24*, Abstract Only,(1980), 10–12.

Chun, S C., et al., "Sodium hypochlorite: effect of solution pH on rice seed disinfestation and its direct effec ton seeding growth", *Plant Dis., 81*, Abstract Only,(1997),821–824.

Cuero, R G., et al., "The influence of gamma irradiation and sodium hypochlorite sterilization on maize seed microflora and germination", *Food Microbiology, 3*, Abstract Only, (1986),107–113.

De, B K., et al., "Effect of dry physiological seed treatments for improved vigor, viability and productivity of black gram (*Phaseolus mungo*)", *Indian Agric., 42*, Abstract only, (1998),13–20.

Dempsey, A H., et al., "Efficacy of calcium and sodium hypochlorite for seed treatment of pepper", *HortScience, 8*, Abstract Only,(1973),328–329.

Dhanvantari, B N., et al., "Improved seed treatments for control of bacterial canker of tomato", *Can. J. Plant Pathol., 15*, Abstract Only,(1993),201–205.

Dhavantari, B N., "Effect of seed extraction methods and seed treatments on control of tomato bacterial canker", *Can. J. Plant Pathol., 11*, Abstract Only,(1989),400–408.

Draughon, F A., et al., "Chemical and biological evaluation of aflatoxin after treatment with sodium hypochlorite, sodium hydroxide and ammonium hydroxide", *J. Food Prot., 45*, Abstract only,(1982),703–706.

Drew, R L., et al., "The effect of sodium hypochlorite on germination of lettuce seed at high temperature", *J. Exp. Bot., 35*, Abstract Only,(1984),975–985.

Drew, R L., et al., "The effects of pH during treatment of lettuce seeds with chlorine–releasing compounds on germination and seedling developments", *Ann. Appl. Biol., 106*, Abstract Only,(1985),157–161.

Dvorak, M, "Possibilities of chemical detoxication of aflatoxin", *Vet. Med., 35*, Abstract only,(1990),37–42.

Elmer, W H., et al., "Comparison of technique for eliminating contaminants from asparagus seeds", *HortScience, 23*, Abstract Only,(1988),1031–1032.

Faifer, G, et al., "Adjustment of the conditions required for complete decontamination of T2 toxin residues with alkaline sodium hypochlorite", *Bull. Environ. Contam. Toxicol., 52*, Abstract only,(1994),102–108.

Feng, D, et al., "Detoxification of aflatoxins in groundnut cake by chemical treatments", *Zhongguo Liangyou Xuebao, 12(2)*, Abstract only,(1997),21–25.

Fresneda, J A., "Sensitivity of six culture media for the detection of Fusarium spp. in seeds", *Ciancias de la Agricultura, 25*, Abstract Only,(1985),7–13.

Goudey, J S., et al., "Effects of hypochlorite disinfection on the response of barley aleurone layers to gibberellic acid", *Physiol. Plant., 69*, Abstract Only,(1987),295–298.

Hasan, "Patulin and aflatoxin in brown rot lesion of apple fruits and their regulation", *World J. Microbiol. Biotechnol., 16(7)*, Abstract only,(2000),607–612.

Homma, Y, et al., "Fungicidal effects of calcium hypochloride on Fusarium wilt pathogens of tomato and cucumber", *Shikoku Shokubutsu Boeki Kenkyu, 12*, Abstract only,(1977), 15–17.

Hsiao, A I., et al., "Induction of germination of skotodormant seeds of Johnson grass, Sorghum halepense (L.) Pers", *Weed Res., 28*, Abstract Only,(1988),163–174.

Hsiao, A I., "The effect of sodium hypochlorite and gibberellic acid on seed dormancy and germination of wild oats (*Avena fatua*)", *Can. J. Bot., 57*, Abstract Only,(1979), 1729–1734.

Hsiao, A I., "The effect of sodium hypochlorite, gibberellic acid, and light on seed dormancy and germination of wild buckwheat (*Polygonum convolvus*) and cow cockle (*Saponaria vaccaria*)", *Can. J. Bot., 57*, Abstract Only, (1979),1735–1739.

Hsiao, A I., et al., "The use of sodium hypochlorite in testing the seed viability of wild oats", *Can. J. Plant. Sci., 59*, Abstract Only,(1979),1047–1052.

Hsiao, A I., et al.,"Wild Oats (*Avena fatua* L.) seed dormancy as influenced by sodium hypochlorite, moist storage and gibberellin A3", *Weed Res., 25*, Abstract Only,(1985), 281–288.

Huang, W Z., et al., "Factors affecting seed dormancy and germination of *Paspalum distichum*", *Weed Res., 27*, Abstract Only,(1987),405–415.

Humaydan, H S., et al., "Eradication of *Zanthomonas campestris*, the causal agent of black rot, from Brassica seeds with antibiotics and sodium hypochlorite", *Phytopathology, 70*, Abstract Only,(1980),127–131.

Igbinnosa, I, et al., "Stimulation of germination of seeds of cowpea witchweed (*Striga gesnerioides*) by sodium hypochlorite and some growth regulators", *Weed Sci., 40*, Abstract Only,(1992),25–28.

James, R L., et al., "Ponderosa pine seed treatments: effects on seed germination and disease incidence", *USDA Forest Service, 81*, Abstract Only,(1981),13.

Ji, M, et al., "Effects of NaOCl on seed germination of Bahiagrass Paspalum notatum Flugge", *Jiangxi Nongye Daxue Xuebao, 22*, Abstract only,(2000),494–497.

Jinno, K, et al., "Calcium hypochlorite as a disinfectant for seeds", *Nogyo Oyobi Engei, 52*, Abstract Only,(1977),1489–1494.

Jinnoh, K, et al., "Application of calcium hypochlorite as a seed disinfectant (a preliminary report)", *Hyogo Kenritsu Nogyo Shikenjo Kenkyu Hokoku, 23*, Abstract Only,(1975),1–8.

Kaiser, W J., et al., "Seed–treatment fungicides for control of seedborne *Ascochyta lentis* on lentil", *Plant Dis., 71*, Abstract Only,(1987),58–62.

Kang, J S., et al., "Effect of hydropriming to enhance the germination in gourd seeds", *Han'guk' Wonye Hakhoechi, 41*, Abstract only,(2000),559–564.

Khah, E M., et al., "Sodium hypochlorite concentration, temperature, and seed age influence germination of sweet pepper", *HortScience, 27*, Abstract Only,(1992),821–823.

Kim, D, et al., "Effects of seed sterilization treatment on germination and seedling growth of bottle gourd (*Lagenaria siceraria*)", *Han'guk Wonye Hakhoechi, 42*, Abstract only,(2001),131–139.

Koponen, H, et al.,"The effect of disinfectants on fungi in pure culture and on different surface materials", *Agric. Sci. Finl., 1(6)*, Abstract only,(1992),587–596.

Ku, J H., et al., "Effect of sodium hypochlorite treatment on germination of spinach seeds", *Han'Guk Wonye Hakhoechi, 37*, Abstract Only,(1996),357–361.

Ku, J H., et al., "Effect of sodium hypochlorite treatment on incidence of seed–borne fungi in several crop seeds", *Nongop Kwahak Yongu, 20*, Abstract Only,(1993),18–24.

Ku, J H., et al., "Stimulation of seed germination of Korean lawn grass (*Zoysia japonica* Steud.) by sodium hypochlorite treatment", *Nongop Kisul Yongu Pogo, 11*, Abstract Only,(1984),201–206.

Laciakova, A, et al., "Chemical detoxication of aflatoxin B1", *Hygiena, 42(1)*, Abstract only,(1997),27–30.

Lang, M M., et al., "Efficacy of novel organic acid and hypochlorite treatments for eliminating *Escherichia coli* 0157:H7 from alfalfa seeds prior to sprouting", *Int. J. Food Microbiol., 58*, Abstract only,(2000),73–82.

Lima, E F., et al., "Comparison of methods of health analysis and occurrence", *Fitopatologia Brasiliera, 7*, Abstract Only,(1982),401–406.

Lo, S, "Effect of sodium hypochlorite treatment on seed–borne organisms and germination of imported vegetable seeds", *Chih Wu Pao Hu Hsueh Hui Hui K'an, 15*, Abstract Only,(1973),147–152.

Mackinnon, P, et al., "An investigation of the degradation of the plant toxin, ricin, by sodium hypochlorite", *Toxicon, 38(2)*, Abstract only,(1999),287–291.

Mallery, C H., et al., "Elimination of bacterial contamination from onion seed", *Plant Physiol, 51*, Abstract Only,(1973),1150–1153.

McDonald, A H., et al., "Germination tests with 'shot' wheat. Effect of treatment for bunt", *Agr. Gax. N.S. Wales, 36*, Abstract only,(1925),414–416.

Mercado, C J., et al., "Chemical detoxification of aflatoxin–containing copra", *J. Food Sci., 56*, Abstract only,(1991),733–735.

Michail, S H., et al., "Detoxification of aflatoxins produced by *Aspergillus flavus*, isolated from paddy grains by using certain natural and chemical materials", *Acta Phytopathol. Entomol. Hung., 29*, Abstract Only,(1994),7–13.

Miche, L, et al., "Effects of rice seed surface sterilization with hypochlorite on inoculated *Burkholderia vietnamiensis*", *Appl. Environ. Microbiol., 67*, Abstract only,(2001),3046–3052.

Mukendi, et al.,"Detoxification of aflatoxin B1 by different chemical methods and evaluation of the efficacy of the treatments applied", *J. Pharm. Belg., 46*, Abstract only,(1991),182–188.

Natarajan, K R., et al., "Destruction of aflatoxins in peanut protein isolates by sodium hypochlorite", *J. Am. Oil Chem. Soc., 52*, Abstract only,(1975),160–163.

Nordin, P, "Preferenetial leaching of pinitol from soybeans during imbibition", *Plant Physiol., 76*, Abstract Only, (1984),313–315.

Oelke, E A., et al, "Influence of chemical seed treatments on germination of dormant wild rice seeds", *Crop Sci., 20*, Abstract Only,(1980),595–598.

Okonkwo, P O., et al., "Aflatoxin B1: simple procedures to reduce levels in tropical foods", *Nutr. Rep. Int., 17*, Abstract only,(1978),387–395.

Okonkwo, S N., et al., "Bleach–induced germination and breakage of dormancy of seeds of *Alectra vogelii*", *Physiol. Plant., 35*, Abstract Only,(1975),175–180.

Papadopoulou, A, et al., "The control of selected micro–organisms during the malting process", *J. Inst.Brew., 106(3)*, Abstract only,(2000),179–188.

Petters, H I., "Influence of formaldehyde and sodium hypochlorite treatment on the malting properties of sorghum", *Global J. Pure Appl. Sci., 4*, Abstract only,(1998),263–267.

Pico, G A., et al., "Kinetics of the aflatoxin B1 –sodium hypochlorite reaction and its application to the study of aflatoxin B1–bovine albumin binding", *Collect. Czech. Chem. Commun., 51*, Abstract only,(1986),2050–2055.

Piernas, V, et al., "Control of microbial growth on rice sprouts", *Int. J. Food Sci. Technol., 33*, Abstract only,(1998),297–305.

Piernas, V, et al., "Disinfection of rice seeds prior to sprouting", *J. Food Sci., 62*, Abstract Only,(1997),611–615.

Pryor, B M., et al., "Detection and eradication of *Alternaria radicina* on carrot seed", *Plant Dis., 78*, Abstract Only, (1994),452–456.

Ramakrishna, N, et al., "Effect of surface sterilization, fumigation and gamma irradiation on the microflora and germination of barley seeds", *International Journal of Food Microbiology, 13*, Abstract Only,(1991),47–54.

Sauer, D B., et al., "Disinfection of seed surfaces with sodium hypochlorite", *Phytopatholgy, 76*, Abstract Only, (1986),745–749.

Schultz, T, et al., "Control of *Xanthomonas campestris* pv. campestris in crucifer seed with slurry treatments of calcium hypochlorite", *Plant Dis., 70*, Abstract Only,(1986),1027–1030.

Shiwaku, K, et al., "Application of calcium hypochlorite as a seed disinfectant", *Hyogo–ken Nogyo Sogo Senta Kenkyu Hokoku, 26*, Abstract Only,(1977),67–74.

Soylemez G, et al., "Microbial quality of alfalfa seeds and sprouts after a chlorine treatment and packaging modifications", *J. Food Sci., 66*, Abstract only,(2001),153–157.

Stevens, J F., et al., "Effects of temperature on decontamination of trichothecene (T–2) mycotoxin using hypochlorite and decontaminating agents D–S2 and STB (supertropical bleach)", *Gov. Rep. Announce, 85*, Abstract only,(1985),22.

Strider, D L., "Eradication of *Xanthomonas nigromaculans* F. sp. zinnae in zinnia seed with sodium hypochlorite", *Plant Dis. Rep., 63*, Abstract Only,(1979),873–876.

Subong, P, et al., "Survey and control of the occurrence of mycotoxins from postharvest cereals: III. Control of mycotoxin producing pathogens in postharvest cereals (what, bean, corn)", *Korean Journal of Plant Pathology, 14*, Abstract Only,(1998),531–536.

Sweet, Haven C., et al., "The surface decontamination of seeds to produce axenic seedlings", *Am. J. Bot., 66*, Abstract Only,(1979),692–698.

Tabata, S, et al., "Degradation of aflatoxins by food additives", *J. Food Prot., 57*, Abstract only,(1994),42–47.

Taormina, P J., et al., "Comparison of chemical treatments to eliminate enterohemorrhagic *Escherichia coli* 0157:H7 on alfalfa seeds", *J. Food Prot., 62*, Abstract only,(1999), 318–324.

Taylor, A G., et al., "Sinapine leakage from Brassica seeds", *J. Am. Soc. Hortic. Sci., 118*, Abstract Only,(1993),546–550.

Toben, H, et al., "Control of umbel blight and seed decay of coriander (Pseudomonas syringae pv. coriandricola)", *Dev. Plant Pathol., 9*, Abstract Only,(1997),611–616.

Trenholm, H L., et al., "A pratical guide to the prevention of *Fusarium mycotoxins* in grain and animal feedstuffs", *Arch. Environ. Contam. Toxicol., 18*, Abstract only,(1989), 443–451.

Umechuruba, C I., et al., "The effects of common disinfectants on seed germination and on seed–borne fungi of African yam bean seeds", *Global J. Pure Appl. Sci., 4*, Abstract only,(1998),9–13.

Velioglu, Y S., et al., "Antioxidant Activity and Total Phenolics in Selected Fruits, Vegatables, and Grain Products", *J. Agric. Food Chem., 46*, Abstract only,(1998),4113–4117.

Ver Kuilen, S D., et al., "Sporicidal action of hypochlorite on conidia of *Aspergillus parasiticus*", *J. Food Prot., 43*, Abstract only,(1980),784–788.

Vieira, H D., et al., "pH and gibberellic acid overcome dormancy of seeds of Brachiaria brizantha cv. Marandu", *Rev. Bras. Fisiol. Veg., 11*, Abstract only,(1999),51–54.

Virk, K S., et al., "Treatment of cut tuber pieces of potato with fungitoxicants to control–decay in autumn sowing", *Journal of the Indian Potato Assocation, 6*, Abstract Only, (1979),109–113.

Vogt, G F., et al.,"Influence of some sterilizing agents on the imbibition aptitude of the Acacia senegal seeds", *Phyton, 31*, Abstract Only,(1991),97–109.

Wang, S, et al., "Effects of mercuric chloride and sodium hypochlorite on germination and seedling growth of cucumber", *Zhiwu Shenglixue Tongxun, 32*, Abstract Only,(1996), 117–120.

Wicks, T J., et al., "Chemical and biological control of Rhizoctonia solani on potato seed tubers", *Aust. J. Exp. Agric., 35*, Abstract Only,(1995),661–664.

Wu, W S., "Sorghum diseases in Taiwan and characterization and control of its seed–borne pathogens", *Plant Protection Bulletin, 25*, Abstract Only,(1983),1–13.

Yang, C Y., "Comparative studies on the detoxification of aflatoxins by sodium hypochlorite and commercial bleaches", *Appl. Microbiol., 24*, Abstract only,(1972), 885–890.

Yoo, Y K., et al., "Changes in phenolics content by development stage, washing, and NaOCl treatment of white forsythia seeds", *Han'Guk Wonye Hakhoechi, 39*, Abstract Only,(1998),193–196.

Yoo, Y K., et al., "Effects of some pretreatments on seed germination of white forsythia (*Abeliophyllum distichum*)", *Han'guk Wonye Hakhoechi, 39*, Abstract only,(1998),86–91.

Young, J C., et al.,"Alkaline degradation of the mycotoxin 4–deoxynivalenol", *Tetrahedron Lett., 27*, Abstract only, (1986),1019–1022.

Young, J C., et al., "Reduction in levels of deoxynivalenol in contaminated wheat by chemical and physical treatment", *J. Agric. Food Chem., 34*, Abstract only,(1986),461–465.

Zachowski, M A., et al., "Reduction of bacterial blight infestation of cotton seeds by treatment with sodium hypochlorite", *J. Phytopathol., 131*, Abstract Only,(1991), 53–38.

Zhang, D, et al., "Factors affecting viscosity of slurries of oat groat flours", *Cereal Chem., 74*, Abstract Only,(1997), 722–726.

\* cited by examiner

PROCESS TO IMPROVE THE QUALITY OF GRAINS AND SEEDS

RELATED APPLICATIONS

This applications claims priority from U.S. Provisional Patent Application No. 60/357,507, filed Feb. 15, 2002, which is incorporated herein by reference.

BACKGROUND OF THE INVENTION

In the past several years, *Fusarium graminearum* contamination has progressively increased in North American crops such that grain yields for barley, wheat and corn have declined substantially, and regulations have been developed to restrict the levels of the toxins in finished food products. The toxins are known to reduce feed intake and weight gain in livestock and to reduce reproductive efficiency. In the past 20 years, plant breeding programs have developed only minor improvements in resistance to either toxin or pathogen effects and so far there is no evidence that fully resistant varieties will emerge in the foreseeable future. An estimated $1 billion was lost in western Minnesota and eastern North Dakota alone during the 1990s due to *Fusarium* infestation. Minnesota agriculture was hit especially hard due to its reliance on the high-yielding Red River Valley production area.

Many grains, especially wheat in the US, are milled into flour. The goal of the milling process is to separate as fully as possible the bran and the germ portion of the wheat kernel from the endosperm. The endosperm is then further reduced into flour. Depending on the color of the type of grain being milled, and the end use of the flour, it may be further processed or bleached. The current process involves the oxidation of the red or yellow pigments in the flour to produce white flour. Oxidization will occur naturally, over time, with the exposure of flour to air. Historically, millers would age flour for several weeks to achieve white flour. This natural oxidation, however, was an irregular process requiring considerable time and space. Today, the bleaching process is accomplished by the use of chemical bleaching agents. Flours treated with these bleaching agents must be labeled as bleached flour.

To date, no method has been developed to treat grains or seeds to effectively aid in reducing the level of fungal contamination and concomitant toxins. Thus, there remains a continuing need for a means to effectively reduce the presence of microbial contaminants in grains and seeds. There is further a long-felt, unresolved need to minimize the presence of microbial toxins in grains and seed. There is also a need for a means to effectively bleach whole grains, rather than bleaching the milled flour. Preferably, such treatments would be environmentally safe.

SUMMARY OF THE INVENTION

The present invention provides a method of treating a grain or seed to reduce the contamination level of seed-associated pathogenic fungi or bacteria or level of a toxin from a seed-associated pathogenic fungi or bacteria by contacting the grain or seed with a solution comprising hypochlorite (sodium or potassium hypochlorite) at a concentration of about 0.1% to about 12% v/v. As used herein the term "reduce the contamination level" means that the presence or level of a fungus, bacteria or toxin is less at the end of the treatment than at the beginning, and the degree to which it is less. Such a reduction may be measured using standard procedures. The reduction may be by 0.1% to 100%, or any value in between, as compared to the level of contamination in the starting material. For example, the reduction may be by 1%, 2%, 3%, 4%, 5%, 10%, 25%, 50%, 80%, 90% or 99.9%.

The present invention also provides a method of increasing lightness of a grain or seed by contacting the grain or seed with a solution comprising hypochlorite at a concentration of about 0.1% to about 12% v/v at the starting pH of above about 5.0 for a period of time. The term "lightness" (or "brightness") is being used as is known in the art. Specifically, this is an indication of a lighter color, in percent, as indicated by the "Y" value in a traditional Yxy scale.

In the methods described above, the hypochlorite can be at a concentration of about 0.5 to about 3.3% v/v, or even at a concentration of about 0.8 to about 1.2% v/v. The starting pH, can be above about 5.0. The starting pH may be at 6.0, 7.0, 8.0, 9.0, or even 13.0, or any pH value in the range between 5.0 and 13.0. The term "starting pH" means the pH of the solution prior to the contacting or introduction of the target grain or seed to the solution. The pH may change as the treatment progresses. Other chemicals may be present in the solution, such as an alkali or acid. Examples include sodium hydroxide, potassium hydroxide, sodium phosphate dibasic, sodium bicarbonate, glacial acetic acid and peracetic acid. The solution may be sprayed, coated, or otherwise spread over the grains or seeds, or alternatively, the grains or seeds may be immersed or soaked in the solution.

In the methods described above, the period of time of the treatment is for at least 1 second. It can be for a period of time from about 1 minute to about 12 hours (or at any time interval in the spectrum between 1 minute to 12 hours), or about 5 minutes to about 5 hours, or about 5 minutes to about 30 minutes. The contacting step can take place at a temperature of about 40 to about 150° F. (or at any temperature between 40° F. and 150° F.), or even at a temperature of about 60 to about 80° F.

The contamination of the grain or seed may be by a fungus, or a toxin from a fungus. Examples of fungi (or their toxins) to be treated include *Fusarium graminearum, Fusarium solani* or other species (*Fusarium* spp.), *Bipolaris sorokiniana, Drechslera teres, Drechslera tritici-repentis, Drechslera avenae* or other species (*Drechslera* spp), *Helminthosporium* spp., *Alternaria* spp., *Diplodia* spp., *Septoria tritici* or other species (*Septoria* spp.), or *Stagonospora nodorum*. Alternatively the contamination of the grain or seed may be by a bacterium, or a toxin from a bacterium. Examples of bacteria (or their toxins) to be treated include *Xanthomonas* spp. or *Pseudomonas* spp. The toxin contaminant may be Deoxynivalenol (DON), Nivalenol, Zearalenone, Trichothecenes, Moniliformin, Fumonisins, Ochratoxin A, Citrinin, or Patulin.

The target grain or seed to be treated by the method of the present invention can be a cereal grain or a seed. Examples of such grains or seeds include wheat (such as red or durum wheat), barley, corn, rice, oats, rye, or soybean, sorghum, peanut, canola, clover, pasture seed, cucurbit seed (such as a watermelon or cucumber), flower seed, or vegetable seed (such as a lettuce, carrot, or tomato). The target product to be treated may be a single type of grain or seed, or may be a mixture of more than one grain or seed. The method of the present invention can increase the germination rate of the grain or seed.

The present invention further provides a grain or seed treated by a process described above. This grain or seed is suitable for human or animal consumption.

DETAILED DESCRIPTION OF THE INVENTION

Figure 1:
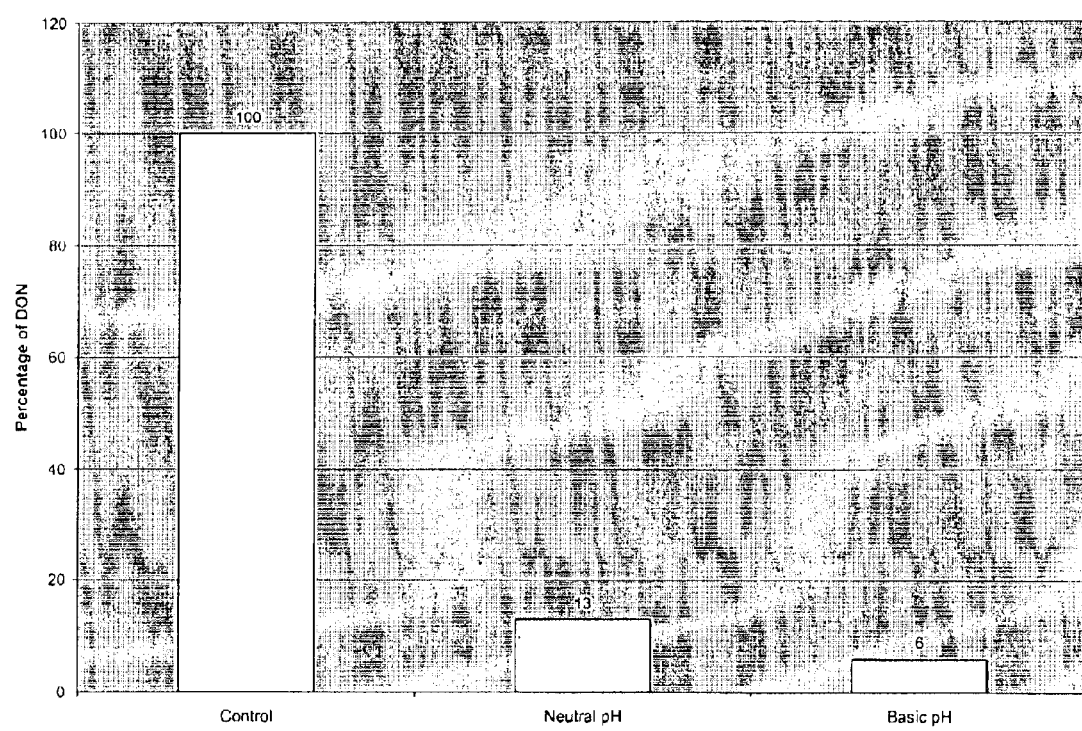
FIG. 1. Reduction of toxin (deoxynivalenol) level in barley seeds after steeping for 7 hours in 0.8% hypochlorite solution under two pH conditions. The toxin level in the control (dry seeds) was 10.9 ppm.

The present inventors have developed a process to reduce or eliminate seed-borne microbes and their toxins that degrade the quality of common agricultural grains and seeds. Examples of these important agricultural products include cereal grains such as barley, corn, and wheat, and legumes such as soy, peas and beans. The process is particularly effective in reducing or eliminating the growth of fungi such as *Fusarium* spp, *Bipolaris* spp, *Pyrenophora* spp and pathogenic bacteria such as *Xanthomonas* spp, and *Pseudomonas*, spp., and in reducing or eliminating the toxins that are produced by these organisms (FIG. 1). The levels of reduction of microorganisms associated with seeds provided by this method is much higher then any other known. The treated seed is thereby made more acceptable for processing such as milling and malting, food manufacturing, for use in animal feeds, and for use as seed treatment to reduce pathogens and improve germination. It is an added feature of the invention that it improves the overall color and related quality characteristics of common grains. This may be of special use in modifying darkly colored cereals (e.g., hard red spring wheats) for enhanced use in common foods (See Tables 20–22 and FIGS. 6–9 below).

Figure 2:
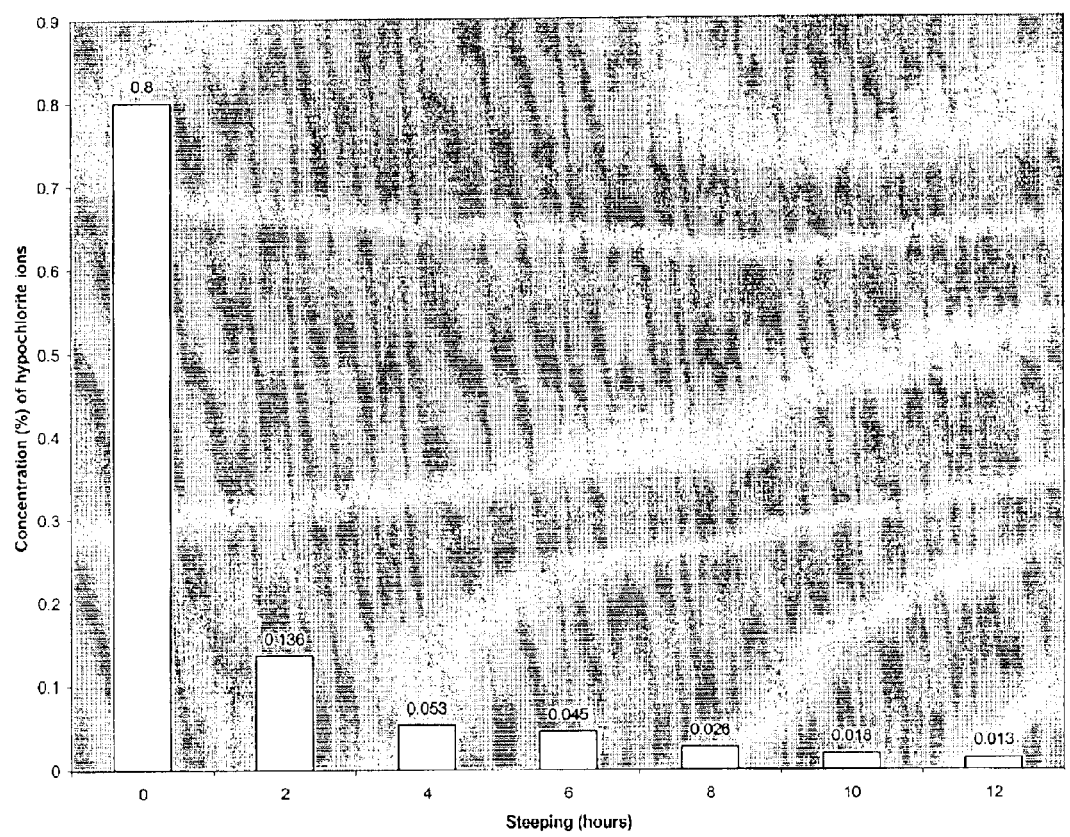
FIG. 2. Concentration (%) of hypochlorite ions leftover in the treatment water after seeds were immersed for different periods of time.

The treatment involves the use of hypochlorite or related ions at carefully controlled concentration, temperature, time, and pH. A typical treatment includes immersion of seed in a solution of 0.8% sodium or calcium hypochlorite and sufficient alkali (such as sodium or potassium hydroxide) in water to maintain the pH between 5.0 and 13.0. The seed remains in the solution for a time sufficient to reduce microbe and toxins to acceptable levels, typically a few minutes to up to about 12 hours. The treated seed is then suitable for most typical food and feed uses, and contains no hypochlorite residues since the ions are soluble in water solution and wash out. After treatment the wet seeds are dried leaving no traces or smell behind. During the treatment, most of the ions in solution react immediately with the surface of fungi, bacteria and seeds, leaving only traces of hypochlorite in the reminiscent (disposable) water solution (FIG. 2).

Other researchers have attempted to reduce the level of the toxin Deoxynivalenol (DON) from wheat seeds using different reagents (See Charmley, L. L. & D. B. Prelusky. 1994. Decontamination of *Fusarium* mycotoxins. In: J. D. Miller & H. L. Trenholm (Eds.). Mycotoxins in grain. Saint Paul, Eagan Press. 1994. 552 pp.). Among the reagents that they tested, sodium hypochlorite (1% concentration) was the only one to increase the level of the toxin in 24% to 1.24 ppm. They postulated that the lack of significant reduction in DON concentration in contaminated wheat under commercial milling and bleaching conditions was likely due to use of low levels of chlorine and relatively short contact times (several minutes).

The significance of this invention lies chiefly in its use to reduce dramatically the levels of both *Fusarium* and its toxins, such as deoxynivalenol (DON), in common grains. The invention also appears to be the only effective method for reclaiming some of the grain that has been downgraded due to toxin or pathogen content, and for improving the rate and uniformity of germination in grains that have been damaged by the infections. It also increases the germination in seeds that exhibit a degree of dormancy.

One of the most important uses of this method is to reduce or remove *Fusarium* and its toxins from malting barley, wheat or corn destined for both human use and for animal feeds, particularly swine, cattle, horses and other animals. In order to evaluate a possible rejection by sensitive animals due to residues or even the smallest smell left on the seeds, barley seeds were treated, formulated into a standard ration, and fed to young pigs for a number of days (See Example 4 below). The animals showed no rejection of ration and ate it at the same rate as the control feed. Other uses include increasing germination in agricultural seeds and malting barley, and improving color and/or flavor in commercial grains.

The present treatment is safe and potentially very inexpensive in commercial applications. The procedure can be easily included as the first step of the typical steeping stage in malting to reduce/remove toxins and fungi such as *Fusarium* spp.

Figure 3:
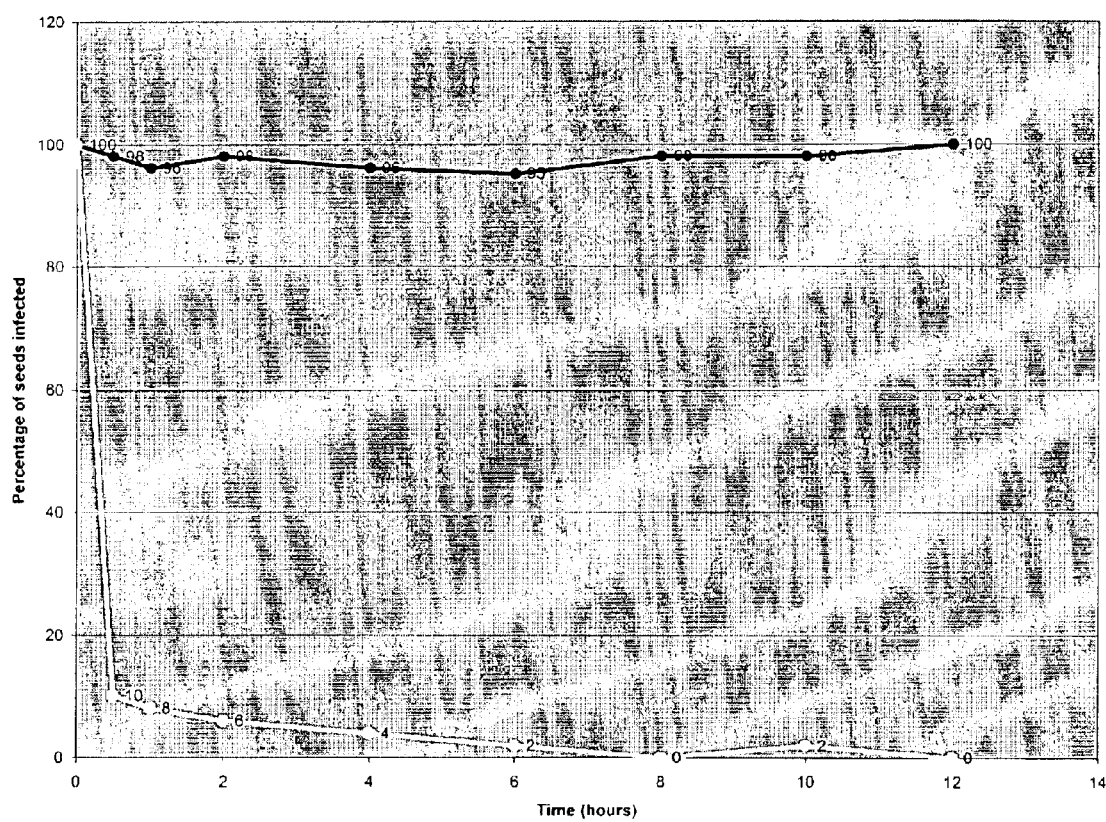
FIG. 3. Percentage of barley seeds contaminated with *Fusarium* after steeping in water (dark line) or in hypochlorite solution (light line) for different periods of time.
Figure 4:
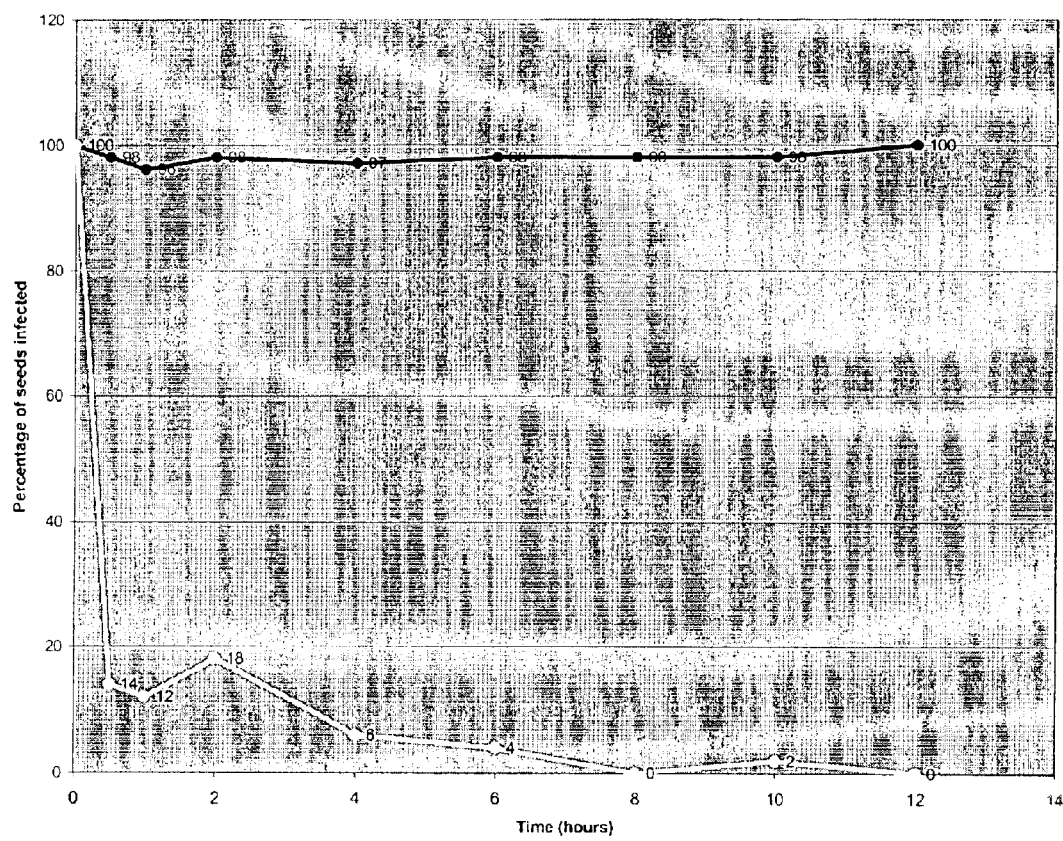
FIG. 4. Percentage of barley seeds contaminated with bacteria after steeping in water (dark line) or in hypochlorite solution (light line) for different periods of time.
Figure 5:
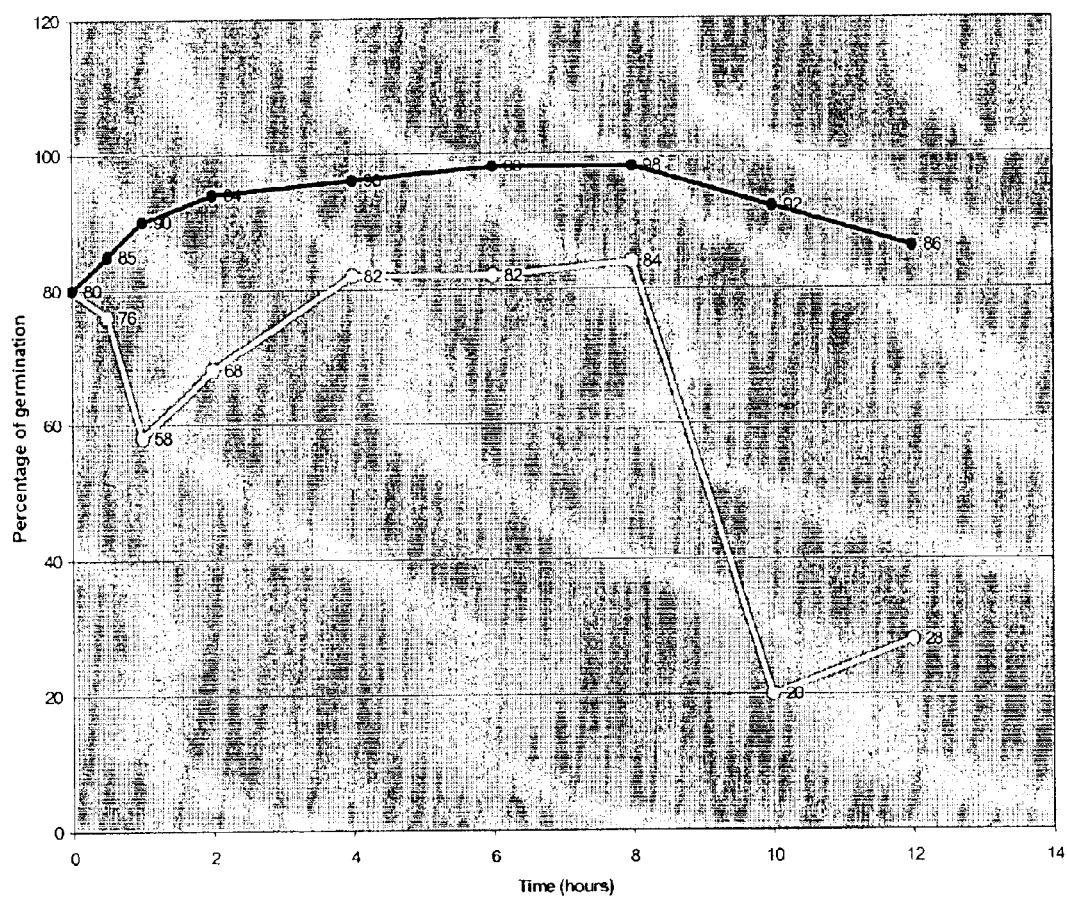
FIG. 5. Germination of barley seeds after steeping in water (dark line) or in hypochlorite solution (light line) for different periods of time.

It has been shown that the process reduced toxin levels by 87–94% (FIG. 1) and *Fusarium* levels by 95–100% (FIG. 3). Also, bacteria levels were reduced between 95–100% (FIG. 4). Germination frequently increased from 70% to 97+% (FIG. 5).

The cost of the treatment is very small (~$1–5/ton) and would be highly beneficial to the malting industry. Malt production in the US alone is at approximately 6.6 billion gallons of malt beverage annually. Malt products in US and Canada utilize approximately 10,000,000 tons of barley per year for malting. However, the use of barley from the upper Midwest has been virtually eliminated in the past few years due to *Fusarium* contamination. American and Canadian barley and malt supplies are at particular risk.

The present invention can be used as a treatment to reduce toxin and microbe contamination in milling wheats prior to flour and semolina production. Midwestern US milling wheat losses have ranged from $200–400 million each year since 1993 with total producer and processor losses well in excess of $1 billion. The USDA currently regulates the levels of the contaminant deoxynivalenol such that a maximum of 2 ppm is allowable in uncleaned wheat destined for the milling trade.

The present invention can be used as a bleaching step for use in the wheat and related milling industries to reduce strong colors and flavors of bran, germ and flour. The industry continues to pursue potential methods for bran and germ bleaching.

The present invention can be used as a feed treatment in the livestock industry to decrease toxins and microorganisms. Depending on the animal, amounts of deoxynivalenol in excess of 5–10 ppm in barley and corn are deemed unusable by the feed industry. Annual losses from these contaminants exceeds are substantial.

The present invention can be used as a fungicide and seed treatment to enhance germination rates in many different types of seeds.

Treatment Conditions

The present invention provides preparing a treatment solution containing hypochlorite. The concentration of hypochlorite can be from about 0.1% to about 12% v/v. It can be at a concentration of about 0.5 and 2.0% v/v or even at about 0.8 and 1.2%. In general, the shorter the treatment time, the more concentrated the solution needs to be.

The treatment solution (prior to contacting the grain or seeds) is at a pH above about 5.0. The starting pH may be at 6.0, 7.0, 8.0, 9.0, or even 13.0, or any pH value in the spectrum between 5.0 and 13.0. NaOH or KOH can be the alkalis used to modify the pH. In one embodiment the solutions is at pH 13 prior putting the seeds in. Soon after the solution starts to work, the pH will usually drop. With an alkali buffer present, however, it will often retain a pH higher than 8.0.

Other chemicals may be present in the solution. Examples include sodium hydroxide, potassium hydroxide, sodium phosphate dibasic, sodium bicarbonate, glacial acetic acid and peracetic acid.

The solution may be sprayed, coated, or otherwise spread over the grains or seeds, or alternatively, the grains or seeds may be immersed or soaked in the solution.

The treatment can be effective at a variety of temperatures. For example, it can take place between about 40° F. and about 150° F. For example, the treatment can take place at a temperature between 50° F. and about 100° F. In one embodiment, it can take place between about 60° F. and 80° F. Ideally these temperatures can be used for malting purposes. Also, for economical reasons, a moderate temperature is desired. It should be noted, however, that the temperature can be increased, if there is a need to speed up the process. This might be of interest for some uses, like improving the color of seeds before processing them.

The treatment process of the present invention is effective against a number of fungi and their toxins. These include the following: *Fusarium graminearum*, *Fusarium solani* and other species (*Fusarium* spp.), *Bipolaris sorokiniana*, *Drechslera teres*, *Drechslera tritici-repentis*, *Drechslera avenae* and other species (*Drechslera* spp), *Helminthosporium* spp., *Alternaria* spp., *Diplodia* spp., *Septoria tritici* and other species (*Septoria* spp.) or *Stagonospora nodorum*. The treatment process of the present invention is effective against a number of plant pathogenic bacteria including *Xanthomonas* spp. and *Pseudomonas* spp.

The treatment process of the present invention is effective against a number of toxins, including Deoxynivalenol (DON), Nivalenol, Zearalenone, Trichothecenes, Moniliformin, Fumonisins, Ochratoxin A, Citrinin, and Patulin.

The process of the present invention can be used to treat a number of target seeds, including wheats (all of them, red, durum, etc.), barley, corn, soybean, rice, oats, rye, sorghum, peanuts, canola, clover, pasture seeds (*Lolium* spp., etc.), cucurbit seeds (watermelon, cucumber, etc.), flower seeds, vegetable seeds (lettuce, carrots, tomato, etc.)

The following examples are intended to illustrate but not limit the invention.

EXPERIMENTAL EXAMPLES

Experimental data for reducing toxins, improving color, killing fungi and bacteria in seeds as well as increasing their germination are presented below.

EXAMPLE 1

Determination of the Best Time and Concentration for Hypochlorite to Control *Fusarium* and Reduce its Toxin in Barley Seeds In this example, the experimental conditions were tested in order to determine the best time and concentration of hypochlorite to control *Fusarium* and to reduce its toxin in barley seeds. The conditions in Table 1 below indicate the initial hypochlorite concentration and the final concentration, the initial pH, and the period of time that the barley was in the solution. In this table, A, B, C, D and E mean hypochlorite concentrations of 0.1, 0.5, 1.0, 2.0 and 4.0% (commercial product) and W mean water steeping only. These results indicate that most of the hypochlorite ions react soon after the seeds are put in contact with the solution. It is also shown that the amounts of the hypochlorite ions left in the solutions after removing the seeds are very small or negligible.

TABLE 1

Chemical conditions of the solutions before and after submitting the barley seeds to the different treatments. Variety used: Lacey.

| Treatments* | Initial conc.* | Time (hour) | pH | Final concentra.* % | Absolute % of hypo. left |
|---|---|---|---|---|---|
| A | 0.1 | 0 | 11.0 | 0.086 | 100% |
| A1 | 0.1 | 4 | 7.2 | 0.011 | 12.8 |
| A2 | 0.1 | 6 | 7.0 | 0.008 | 9.3 |
| A3 | 0.1 | 8 | 6.8 | 0.005 | 5.8 |
| A4 | 0.1 | 10 | 6.7 | 0.005 | 5.8 |
| A5 | 01 | 12 | 6.6 | 0.005 | 5.8 |
| B | 0.5 | 0 | 11.7 | 0.392 | 100 |
| B1 | 0.5 | 2 | 8.1 | 0.067 | 17.1 |
| B2 | 0.5 | 4 | 7.6 | 0.026 | 6.6 |
| B3 | 0.5 | 6 | 7.3 | 0.022 | 5.6 |
| B4 | 0.5 | 8 | 6.9 | 0.013 | 3.3 |
| B5 | 0.5 | 10 | 6.8 | 0.013 | 3.3 |

TABLE 1-continued

Chemical conditions of the solutions before and after submitting the barley seeds to the different treatments. Variety used: Lacey.

| Treatments* | Initial conc.* | Time (hour) | pH | Final concentra.* % | Absolute % of hypo. left |
|---|---|---|---|---|---|
| B6 | 0.5 | 12 | 6.7 | 0.013 | 3.3 |
| C | 1.0 | 0 | 11.9 | 0.818 | 100 |
| C1 | 1.0 | 2 | 8.3 | 0.224 | 27.4 |
| C2 | 1.0 | 4 | 8.0 | 0.081 | 9.9 |
| C3 | 1.0 | 6 | 7.9 | 0.016 | 1.9 |
| C4 | 1.0 | 8 | | | |
| C5 | 1.0 | 10 | 6.8 | 0.019 | 2.3 |
| C6 | 1.0 | 12 | 6.8 | 0.013 | 1.6 |
| D | 2.0 | 0 | 12.1 | 1.62 | 100 |
| D1 | 2.0 | 0.5 | 9.2 | 1.14 | 70.3 |
| D2 | 2.0 | 1 | 8.8 | 0.89 | 54.9 |
| D3 | 2.0 | 2 | 8.56 | 0.59 | 36.4 |
| D4 | 2.0 | 4 | 8.0 | 0.21 | 12.9 |
| D5 | 2.0 | 6 | 7.8 | 0.14 | 8.6 |
| D6 | 2.0 | 8 | 6.2 | 0.027 | 1.6 |
| E | 4.0 | 0 | 12.4 | 3.35 | 100 |
| E1 | 4.0 | 0.5 | 9.4 | 2.56 | 76.4 |
| E2 | 4.0 | 1 | — | | |
| E3 | 4.0 | 2 | 7.9 | 0.97 | 28.9 |
| E4 | 4.0 | 4 | 6.8 | 0.08 | 2.3 |
| E5 | 4.0 | 6 | 7.0 | 0.04 | 1.2 |
| E6 | 4.0 | 8 | 6.6 | 0.032 | 0.9 |
| W | | 0 | 7.0 | | |
| W1 | | 0.5 | | | |
| W2 | | 1.0 | | | |
| W3 | | 2.0 | | | |
| W4 | | 4.0 | | | |
| W5 | | 6.0 | | | |
| W6 | | 8.0 | | | |
| W7 | | 10.0 | | | |
| W8 | | 12.0 | 6.2 | | |

*A, B, C, D and E mean hypochlorite concentrations of 0.1, 0.5, 1.0, 2.0 and 4.0% (commercial product, except in the "final concentration column"), and W stands for water alone.

After the barley was treated, experiments were performed to determine if the barley was still capable of germination, and whether or not *Fusarium graminearum* and/or bacteria were still present on the seeds. In addition, the level of toxin was tested. The results are provided in Table 2. Evaluation was done five days after plating the seeds to PDA growth medium on 50 seeds per treatment.

These results indicate that the best combined effects for increasing germination and reducing *Fusarium* and bacteria from seeds was leaving the seeds in the solution containing 0.8% hypochlorite for 8 hours.

TABLE 2

Mean of germination and microorganisms (*Fusarium graminearum* and bacteria) associated to the barley seeds and levels of toxin (DON) after steeping in hypochlorite solution varying in concentration and time.

| Treat. | Time (hour) | Germin. (%) | Fusarium (%) | Bacteria (%) | DON μg/ml | % DON variation from steeping | Total % of DON reduction |
|---|---|---|---|---|---|---|---|
| A1 | 4 | 72 | 20* | 94 | 4.0 | +11.1 | −63.3 |
| A2 | 6 | 84 | 14* | 100 | 3.4 | +6.2 | −68.8 |
| A3 | 8 | 92 | 28* | 100 | 3.3 | +22.2 | −69.7 |
| A4 | 10 | 76 | 20* | 100 | 2.2 | −12.0 | −79.8 |
| A5 | 12 | 82 | 16* | 100 | 1.9 | −26.9 | −82.5 |
| B1 | 2 | 70 | 18 | 40 | 5.4 | +17.4 | −50.4 |
| B2 | 4 | 90 | 8 | 24 | 4.6 | +27.7 | −57.8 |
| B3 | 6 | 90 | 2 | 32 | 2.9 | −9.4 | −73.4 |
| B4 | 8 | 88 | 4 | 16 | 2.2 | −18.5 | −79.8 |
| B5 | 10 | 72 | 8 | 32 | 1.5 | −40.0 | −86.2 |
| B6 | 12 | 76 | 4 | 12 | 1.8 | −30.7 | −83.5 |
| C1 | 2 | 80 | 10 | 18 | 4.1 | −10.8 | −62.4 |
| C2 | 4 | 84 | 6 | 6 | 4.0 | +11.1 | −63.3 |
| C3 | 6 | 80 | 6 | 14 | 2.0 | −37.0 | −81.6 |
| C4 | 8 | 82 | 4 | 6 | 1.6 | −40.7 | −85.3 |
| C5 | 10 | 76 | 2 | 10 | 1.6 | −36.0 | −85.3 |
| C6 | 12 | 74 | 6 | 12 | 1.4 | −46.1 | −87.1 |
| D1 | 0.5 | 84 | 10 | 30 | 5.4 | −19.5 | −50.4 |
| D2 | 1 | 82 | 12 | 12 | 6.1 | +10.9 | −44.0 |
| D3 | 2 | 64 | 6 | 22 | 3.9 | −15.2 | −64.2 |
| D4 | 4 | 52 | 0 | 2 | 2.5 | −30.5 | −77.0 |
| D5 | 6 | 30 | 2 | 4 | 1.6 | −50.0 | −85.3 |
| D6 | 8 | 32 | 4 | 0 | 1.4 | −48.1 | −87.1 |
| E1 | 0.5 | 78 | 14 | 14 | 7.0 | +4.5 | −35.8 |
| E2 | 1 | 68 | 8 | 22 | 3.3 | −40.0 | −69.7 |
| E3 | 2 | 10 | 2 | 0 | 2.0 | −56.5 | −81.6 |
| E4 | 4 | 4 | 0 | 0 | 0.7 | −80.5 | −93.6 |
| E5 | 6 | 0 | 2 | 0 | 0.4 | −87.5 | −96.3 |
| E6 | 8 | 6 | 0 | 0 | 0.4 | −85.2 | −96.3 |
| W1 | 0.5 | 76 | 98 | 100 | 6.7 | 100 | −38.5 |
| W2 | 1.0 | 58 | 96 | 100 | 5.5 | 100 | −49.5 |
| W3 | 2.0 | 68 | 98 | 100 | 4.6 | 100 | −57.8 |
| W4 | 4.0 | 82 | 96 | 92 | 3.6 | 100 | −67.0 |
| W5 | 6.0 | 82 | 95 | 100 | 3.2 | 100 | −70.6 |
| W6 | 8.0 | 84 | 98 | 100 | 2.7 | 100 | −75.2 |
| W7 | 10.0 | 20 | 98 | 94 | 2.5 | 100 | −77.0 |
| W8 | 12.0 | 28 | 100 | 100 | 2.6 | 100 | −76.1 |
| Dry seeds | | 74 | 80 | 72 | 10.9 | | 100 |
| Desinf. seeds | | 62 | 20 | 86 | | | |

A, B, C, D and E mean hypochlorite concentrations of 0.1, 0.5, 1.0, 2.0 and 4.0% (commercial product) and W stands for water alone.
*Too many bacteria colonies.

EXAMPLE 2

Testing Other Chemicals in Combination with Hypochlorite

This experiment tested whether it was beneficial to add additional chemicals to the hypochlorite solution. The time used in this test was 8 hours. After the barley was treated, experiments were performed to determine if the barley was still capable of germination, and whether or not *Fusarium graminearum* and/or bacteria were still present on the seeds. Evaluation was done by plating 50 seeds per treatment onto PDA growth medium. Also, the level of toxin (DON) was tested after the treatments. The results are provided in Tables 3 and 4.

These results indicate that the combination of the compounds sodium hydroxide, glacial acetic acid and peracetic acid to the hypochlorite solution can improve the performance of hypochlorite solution. By far most of the effect, however, is due to the hypochlorite solution alone. It should be noticed that the other chemicals alone do not provide good results.

TABLE 3

Mean of germination and microorganisms (*Fusarium graminearum* and bacteria) associated to the barley seeds and levels of toxin (DON) after steeping in hypochlorite solution alone or in combination with other chemicals at different concentrations.
Initial and final pH data are provided.

| Treatments | pH initial | pH final | Germin. (%) | Fusarium (%) | Bacteria (%) | DON µg/ml | Total % of DON reduction |
|---|---|---|---|---|---|---|---|
| 1. Eth. Ac. 1% | 6.1 | 5.2 | 6 | 88 | 90 | 3.5 | 68 |
| 2. Eth. Ac. 1% + H | 11.6 | 6.7 | 26 | 0 | 4 | | |
| 3. Eth. Ac. 10% | 4.7 | 4.7 | 0 | 0 | 4 | 3.3 | 70 |
| 4. Eth. Ac. 10% + H | 10.2 | 6.5 | 0 | 0 | 0 | 2.5 | 77 |
| 5. Salt 1% | 6.0 | 6.2 | 72 | 90 | 76 | 3.1 | 71 |
| 6. Salt 1% + H | 11.6 | 6.8 | 80 | 6 | 6 | 2.2 | 80 |
| 7. Salt 5% | 6.0 | 6.3 | 80 | 84 | 78 | 2.5 | 77 |
| 8. Salt 5% + H | 11.6 | 6.7 | 76 | 4 | 8 | 2.2 | 80 |
| 9. Alco. 1% | 5.9 | 6.4 | 72 | 94 | 94 | 3.4 | 69 |
| 10. Alco. 1% + H | 11.7 | 7.2 | 78 | 10 | 0 | 2.1 | 81 |
| 11. Alco. 10% | 5.7 | 6.8 | 2 | 44* | 100 | 2.8 | 74 |
| 12. Alco. 10% + H | 11.8 | 8.1 | 6 | 4 | 16 | 2.9 | 73 |
| 13. Water | 6.7 | 6.3 | 78 | 98 | 100 | | |
| 14. H in vacuum | | | 78 | 92 | 90 | | |
| 15. Dry seeds | | | | | | 10.9 | |

*too many colonies of bacteria.
Eth. Ac. = Ethyl Acetate
Salt = NaCl
Per. ac. = Peracetic acid
Alco. = Alcohol
H = hypochlorite 0.8%
The time for steeping the seeds in the solutions was 8 hours.

TABLE 4

Initial and final ph of treatment solutions and mean of germination and microorganisms (*Fusarium graminearum* and bacteria) associated to the barley seeds and levels of toxin (DON) after steeping in hypochlorite solution alone or in combination with other chemicals.

| Treatments | pH initial. | pH final | Germin. (%) | Fusarium (%) | Bacteria (%) | DON µg/ml | Total % of DON reduction |
|---|---|---|---|---|---|---|---|
| 1. Hypochlorite 0.8% | 11.9 | 7.1 | 80 | 2 | 2 | 1.2 | 87.6 |
| 2. NaOH 0.1% | 12.4 | 10.0 | 76 | 76 | 74 | 2.5 | 74.2 |
| 3. NaOH 0.1% + H | 12.5 | 8.2 | 82 | 4 | 10 | 2.2 | 77.3 |
| 4. NaOH 0.25% | 12.8 | 7.3 | 96 | 88 | 80 | 4.3 | 55.6 |
| 5. NaOH 0.25% + H | 12.9 | 9.6 | 96 | 4 | 4 | 2.0 | 79.4 |
| 6. NaOH 0.5% | 13.0 | 8.7 | 88 | 68 | 50 | 3.8 | 60.8 |
| 7. NaOH 0.5% + H | 13.1 | 11.2 | 98 | 6 | 4 | 1.4 | 85.5 |
| 8. NaOH 1.0% | 13.3 | 12.9 | 66 | 2 | 6 | 0.6 | 94.0 |
| 9. NaOH 1.0% + H | 13.3 | 12.7 | 54 | 0 | 0 | 0.6 | 94.0 |
| 10. H$_2$O$_2$ 1.0% | 5.2 | 6.4 | 94 | 38 | 47 | 3.3 | 66.0 |
| 11. H$_2$O$_2$ 1.0% + H | 10.4 | 7.0 | 92 | 36 | 23 | 2.8 | 71.1 |
| 12. H$_2$O$_2$ 3.0% | 4.5 | 6.4 | 92 | 20 | 62 | 2.3 | 76.3 |
| 13. H$_2$O$_2$ 3.0% + H | 9.2 | 6.8 | 96 | 0 | 60 | 2.3 | 76.3 |
| 14. Ac. Ac. Glacial 0.25% | 3.2 | 4.3 | 64 | 2 | 6 | 2.8 | 71.1 |
| 15. Ac. Ac. Glacial 0.25% + H | 8.0 | 6.1 | 86 | 2 | 0 | 2.3 | 76.3 |
| 16. Ac. Ac. Glacial 0.5 | 2.8 | 4.1 | 8 | 4 | 2 | 3.6 | 62.9 |
| 17. Ac. Ac. Glacial 0.5% + H | 5.3 | 5.2 | 70 | 4 | 0 | 3.5 | 64.0 |
| 18. Ac. Ac. Glacial 1.0 | 2.8 | 3.8 | 0 | 2 | 0 | 2.8 | 71.1 |
| 19. Ac. Ac. Glacial 1.0% + H | 4.5 | 4.7 | 10 | 0 | 0 | 2.2 | 77.3 |
| 20. Ac. Perac. 0.1% | 4.1 | 5.1 | 94 | 56 | 48 | 2.0 | 79.4 |
| 21. Ac. Perac. 0.1 + H | 9.3 | 6.7 | 88 | 2 | 0 | 1.3 | 86.6 |
| 22. Ac. Perac. 0.25% | 4.1 | 4.7 | 76 | 2 | 62 | 3.3 | 66.0 |
| 23. Ac. Perac. 0.25 + H | 8.2 | 6.3 | 80 | 6 | 0 | 2.8 | 71.1 |
| 24. Ac. Perac. 0.5% | 4.1 | 4.5 | 28 | 4 | 28 | 2.8 | 71.1 |
| 25. Ac. Perac. 0.5% + H | 7.8 | 5.6 | 70 | 0 | 0 | 2.1 | 78.3 |
| 26. Ac. Perac. 1.0% | 6.3 | 4.8 | 0 | 4 | 4 | 2.6 | 76 |
| 27. Ac. Perac. 1.0% + H | 9.3 | 6.7 | 88 | 2 | 0 | 1.3 | 86.6 |

TABLE 4-continued

Initial and final ph of treatment solutions and mean of germination and microorganisms (*Fusarium graminearum* and bacteria) associated to the barley seeds and levels of toxin (DON) after steeping in hypochlorite solution alone or in combination with other chemicals.

| Treatments | pH initial. | pH final | Germin. (%) | Fusarium (%) | Bacteria (%) | DON µg/ml | Total % of DON reduction |
|---|---|---|---|---|---|---|---|
| 28. Ac. Perac. 2.0% | 4.0 | 4.2 | 0 | 2 | 0 | 3.1 | 71 |
| 29. Ac. Perac. 2.0% + H | 4.6 | 4.5 | 0 | 0 | 2 | | |
| 30. Water | 5.9 | 6.5 | 86 | 84 | 68 | 2.3 | 76.3 |
| 31. Dry seeds | | | 88 | 78 | 88 | 9.7 | 0 |
| 32. Desinf. With H/2 min | 11.9 | 11.8 | 84 | 16 | 66 | 8.3 | 14.4 |

*Treatments: NaOH (sodium hydroxide), $H_2O_2$ (peroxide), Ac. Ac. Glacial (glacial acetic acid), Ac. Perac (peracetic acid), H (hypochlorite 0.8%).
Obs. Treatments 11 and 19 were too bad, showing many fungi other than *Fusarium graminearum*.

It should be pointed out that by disinfesting the seeds used in the experiments shown in Tables 3 and 4 (variety Lacey, 10.9 ppm of DON) with hypochlorite solution (0.8%) for 2 or 3 minutes (practice routinely done in phytopathological labs), there was an increase in the number of *Alternaria* sp. fungus. Also there was a reduction in the number of colonies of *Fusarium graminearum*. This is in accordance with the literature, which shows almost no effect of hypochlorite in controlling *Alternaria* fungi as well as showing that hypochlorite is capable to reduce *Fusarium graminearum* to some extent only. The present inventors performed an experiment to confirm this, and the data is presented in Table 5 below. In the literature there are only few reports relating *Fusarium* reduction from seeds due to hypochlorite and even so they were never higher then 50%. There were also reports saying that solutions do not reduce the number of infected seeds after treatment. What is not found in the literature, however, is a description of a different, novel method in preparing and using hypochlorite solutions that almost eradicating the fungus from the seeds.

TABLE 5

Percentage of *Alternaria* e *Fusarium* in barley seeds (var. Lacey) disinfested for 2 or 3 minutes in hypochlorite solution (0.8%).

| Treatments | % of *Alternaria* spp. | % of *Fusarium graminearum* |
|---|---|---|
| 2 min. disinfestations | 66 | 20 |
| 3 min. disinfestations | 68 | 18 |

EXAMPLE 3

The Effect of some Alkali Compounds in Regulating the pH in the Hypochlorite Solution and Maximizing Microorganisms Control and Germination In the following experiment, the effect of some alkali compounds in regulating the pH in the hypochlorite solution and maximizing microorganisms control and germination was determined. The bases used were the following: sodium hydroxide, potassium hydroxide, sodium phosphate dibasic and sodium bicarbonate.

TABLE 6

Effect of pH regulators in controlling microorganisms and improving germination of barley seeds when associated with hypochlorite solution (0.8%). The numbers (percentage) are means of 50 seeds plated in ¼ PDA medium.

| Treatments | Initial pH | Final pH | % Germination | % Fusarium | % Bacteria |
|---|---|---|---|---|---|
| 1. Dry seeds (control) | | | 90 | 86 | 64 |
| 2. Hypochlorite 0.8% (control) | 11.9 | 7.1 | 88 | 8 | 0 |
| 3. NaOH (0.25%) | 12.5 | 11.6 | 94 | 44 | 44 |
| 4. NaOH (0.5%) | 12.7 | 12.4 | 96 | 40 | 8 |
| 5. NaOH (0.25%) + Hypochlorite 0.8%* | 12.2 | 9.2 | 96 | 10 | 8 |
| 6. NaOH (0.5%) + Hypochlorite 0.8%* | 12.6 | 10.6 | 94 | 4 | 16 |
| 7. KOH (0.25%) | 12.4 | 10.5 | 94 | 76 | 82 |
| 8. KOH (0.5%) | 12.7 | 12.0 | 96 | 44 | 44 |
| 9. KOH (0.25%) + Hypochlorite 0.8%* | 12.1 | 8.6 | 96 | 6 | 16 |
| 10. KOH (0.5%) + Hypochlorite 0.8%* | 12.5 | 9.6 | 100 | 12 | 8 |
| 11. $Na_2HPO_4$ (0.25%) | 8.3 | 7.3 | 98 | 68 | 68 |
| 12. $Na_2HPO_4$ (0.5%) | 9.2 | 7.5 | 94 | 70 | 72 |
| 13. $Na_2HPO_4$ (0.25%) + Hypochlorite 0.8% | 10.1 | 7.3 | 88 | 8 | 4 |
| 14. $Na_2HPO_4$ (0.5%) + Hypochlorite 0.8% | 10.0 | 7.4 | 84 | 12 | 8 |
| 15. $NaHCO_3$ (0.25%) | 8.1 | 7.3 | 90 | 52 | 70 |
| 16. $NaHCO_3$ (0.5%) | 8.3 | 7.6 | 88 | 72 | 84 |
| 17. $NaHCO_3$ (0.25%) + Hypochlorite 0.8% | 9.5 | 7.3 | 82 | 6 | 4 |
| 18. $NaHCO_3$ (0.5%) + Hypochlorite 0.8% | 9.2 | 7.5 | 88 | 4 | 4 |

*Best combinations for all the effects combined. The general aspects of these plates were very good with germinated seeds showing good size of roots and first leaf. Also, these treatments showed much lower amounts of other fungi (such as Alternaria, Penicilium, Aspergillus, etc.)

The conclusion is that, among the alkali substances, NaOH was the best substance to mix with hypochlorite followed by KOH (potassium hydroxide) which was almost as good as NaOH (sodium hydroxide) in keeping the pH high and maintaining the same biological activity as NaOH does in the hypochlorite solution. The other two substances tested $Na_2HPO_4$ (phosphoric acid) and $NaHCO_3$ (sodium bicarbonate) did not improve the performance of hypochlorite when in combination with it.

EXAMPLE 4

Choice Experiment (Rejection or Acceptance) of Ration Prepared with Barley Submitted to the Hypochlorite Treatment The following tests were made using piglets at the University of Minnesota. The pigs were fed seeds (Var. Lacey) that were either (A) processed seeds (hypochlorite treatment) (4.104 kg) or (B) non-processed seeds (4.104 kg). The evaluations were for (1) preference and/or rejection and (2) rate of consumption of rations. The results indicate that the pigs ate both rations at the same ratio showing no rejection for the processed seeds (A).

TABLE 7

Choice experiment for Diet A and B during 4 days with 6 small pigs.

| | Barley A | | Barley B | |
|---|---|---|---|---|
| Pig No | Add-Leftover | Feed intake | Add-Leftover | Feed intake |
| 1 | 1600–360 | 1240 | 1520–260 | 1260 |
| 2 | 1600–420 | 580 | 1000–100 | 900 |
| 3 | 1000–360 | 640 | 2280–500 | 1780 |
| 4 | 1600–10 | 1500 | 1000–320 | 680 |
| 5 | 1000–120 | 880 | 1000–220 | 780 |
| 6 | 1000–140 | 860 | 1000–240 | 760 |
| Σ | | 5700 | | 6160 |
| Means/pig | | 950 | | 1026.7 |
| ADFI* | | 237.5 ns | | 256.7 ns |
| Σ** | | 3620 | | 3700 |
| Means/pig | | 905 | | 925 |
| ADFI* | | 226.3 ns | | 231.3 ns |

**After delete highest and lowest feed intakes.
*ADFI (average daily feed intake).
ns = not statistically different.

EXAMPLE 5

DON Variation During the Malting Process

The goal of this experiment was to follow the main steps of malt production for DON increase or decrease when barley seeds were submitted to the hypochlorite process during the first steeping, compared with the same seed not submitted to the hypochlorite process. Two samples of 1000 grams of barley seeds infected with 3.2 ppm of DON were malted and their DON contents were measured during the following steps:

Treatments (steps):
1. On 50 grams of seeds just after the first steeping (7 hours steep)
2. On 50 grams of seeds just after the second steeping (5 hours steep)
3. On 50 grams of seeds on the second day of malting (half malting)
4. On 50 grams of seeds on the fourth day of malting (end of malting)
5. On 50 grams of seeds after the fist step of kilning (6 hours at 45° C.)
6. On 50 grams of seeds after the second step of kilning (3 hours at 65° C.)
7. On 50 grams of seeds after the third step of kilning (2 hours at 85° C.)
8. Control (dry seeds without treatment).

The results from Table 8 show a highly significant reduction in the toxin content (78.1%) in the seeds that were submitted to the first steeping in the hypochlorite solution compared with the seep in water alone (46.8% toxin reduction only). In all the subsequent steps during the malting process the seeds that were submitted to the hypochlorite treatment also showed significant reductions in toxin in relation to the non-treated seeds.

TABLE 8

Levels of DON (ppm) during the malting process when contaminated barley seeds were submitted to the hypochlorite (H) process.

| Steps in the malting process | DON levels on Control (a) | % DON reduction | DON levels on "H" process (b) | % DON reduction |
|---|---|---|---|---|
| 1. After the first steeping | 1.7 | 46.8 | 0.7 | 78.1 |
| 2. After the second steeping | 0.5 | 84.3 | 0.4 | 87.5 |
| 3. Second day of malting | 0.6 | 81.2 | 0.4 | 87.5 |
| 4. Fourth day of malting | 0.7 | 78.1 | 0.4 | 87.5 |
| 5. Fist step of kilning | 0.7 | 78.1 | 0.3 | 90.6 |
| 6. Second step of kilning | 0.7 | 78.1 | 0.3 | 90.6 |
| 7. Third step of kilning | 0.7 | 78.1 | 0.4 | 87.5 |
| 8. Control | | 3.2 | | |

EXAMPLE 6

Seed Color Improvement

Seeds of wheat (*Triticum aestivum*) and durum wheat (*Triticum durum*) were tested to determine seed color improvement. Color values were obtained using a Minolta C100 Chroma Meter. Numerical values were expressed in the "Yxy" color system. In this system Y values relate to "lightness" (i.e. higher "Y" indicates lighter color, in percent), while x and y are indicators of color tone. In these treated wheat samples, for example, a decrease in "x" indicates reduced red color.

In the first experiment (Table 9), the seeds were left in solutions (steeped) with different concentrations of hypochlorite or hypochlorite+NaOH for 1 hour. The concentration used for NaOH was 0.25%. After steeping the seeds were dried and grinded to measure their color values (Y and x) as well as their percentage of aleurone and pericarp. In the second experiment (Table 10), only seeds of red wheat were tested for color improvement when submitted to different solutions varying in concentration and time. The most important aspects of the color, lightness and redness, were measured and compared with one control treatment that was a white wheat.

TABLE 9

Effect of chemical treatments on seed color values, percentage of aleurone and pericarp in wheat, durum wheat, corn and soybean. Each number in the % of aleurone and pericarp column represents the mean of 390 microscope fields.

| | Color values** | | | |
|---|---|---|---|---|
| Treatments* | Lightness (Y) | Redness (x) | Aleurone (%) | Pericarp (%) |
| 1. *Triticum durum* dry (control). | 63.9275 | 0.34785 | 11.46 | 1.80 |
| 2. *Triticum durum* in water. | 64.4075 | 0.34695 | 11.23 | 1.71 |
| 3. *Triticum durum* in H 0.8%. | 71.0025 | 0.3462 | 10.87 | 1.58 |

TABLE 9-continued

Effect of chemical treatments on seed color values, percentage of aleurone and pericarp in wheat, durum wheat, corn and soybean. Each number in the % of aleurone and pericarp column represents the mean of 390 microscope fields.

| Treatments* | Color values** | | Aleurone (%) | Pericarp (%) |
| --- | --- | --- | --- | --- |
| | Lightness (Y) | Redness (x) | | |
| 4. *Triticum durum* in H 0.8%. + NaOH | 69.6 | 0.348875 | 11.55 | 4.05 |
| 5. *Triticum durum* in H 1.6%. | 70.6825 | 0.344525 | 10.41 | 2.31 |
| 6. *Triticum durum* in H 1.6%. + NaOH | 70.0375 | 0.3483 | 11.45 | 4.43 |
| 7. *Triticum aestivum* dry (control). | 64.3325 | 0.336875 | 9.85 | 3.64 |
| 8. *Triticum aestivum* in water. | 64.87 | 0.335775 | 9.71 | 2.72 |
| 9. *Triticum aestivum* in H 0.8%. | 70.51 | 0.334975 | 9.49 | 4.06 |
| 10. *Triticum aestivum* in H 0.8%. + NaOH | 69.26 | 0.3346 | 10.07 | 6.26 |
| 11. *Triticum aestivum* in H 1.6%. | 72.8125 | 0.33305 | 8.95 | 4.66 |
| 12. *Triticum aestivum* in H 1.6%. + NaOH | 70.465 | 0.333975 | 9.80 | 6.10 |

*where H means hypochlorite.
**Color values were obtained using a Minolta C100 Chroma Meter. Numerical values were expressed in the "Yxy" color system where Y relates to "lightness", in percent and x indicates reduced red color. Numbers are means of four replications.

Figure 6:
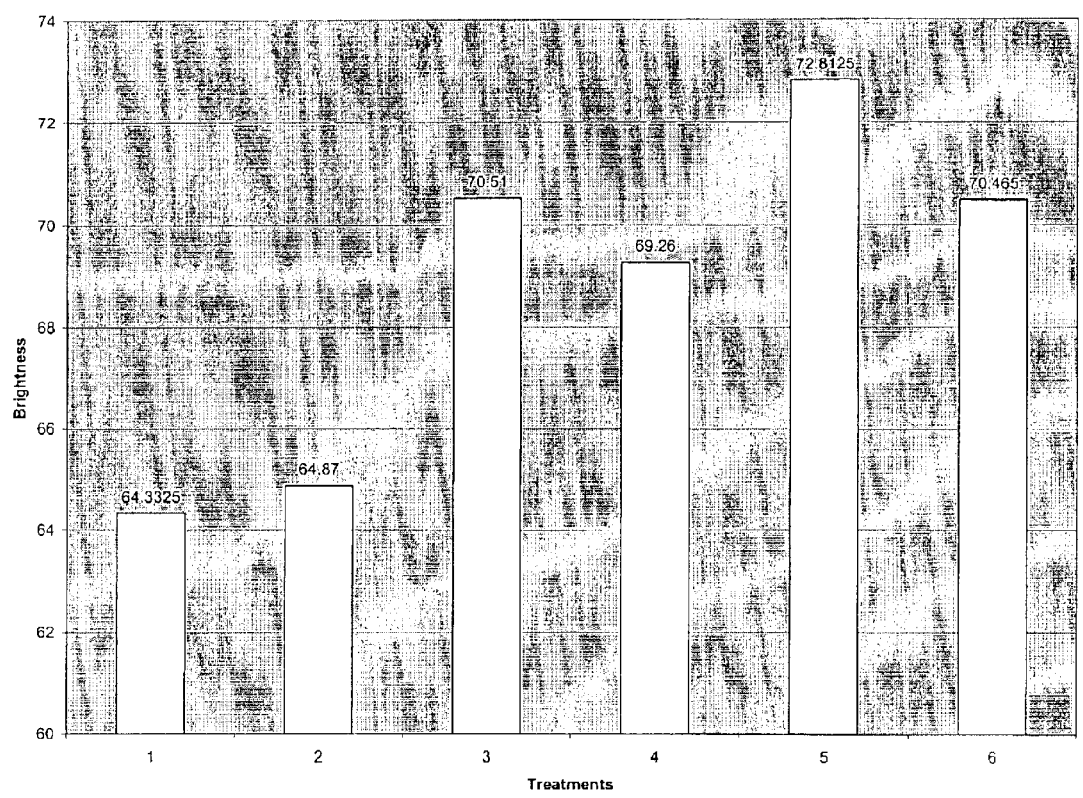
FIG. 6. Increase in the lightness color of red wheat after treating the seeds with hypochlorite. Treatments are: 1=Dry seeds (red wheat control); 2=Water steep; 3=Hypochlorite 0.8%; 4=Hypochlorite 0.8%+NaOH; 5=Hypochlorite 1.6%; 6=Hypochlorite 1.6%+NaOH. The time used was 1 hour and the sodium hydroxide concentration was 0.25%.
Figure 7:
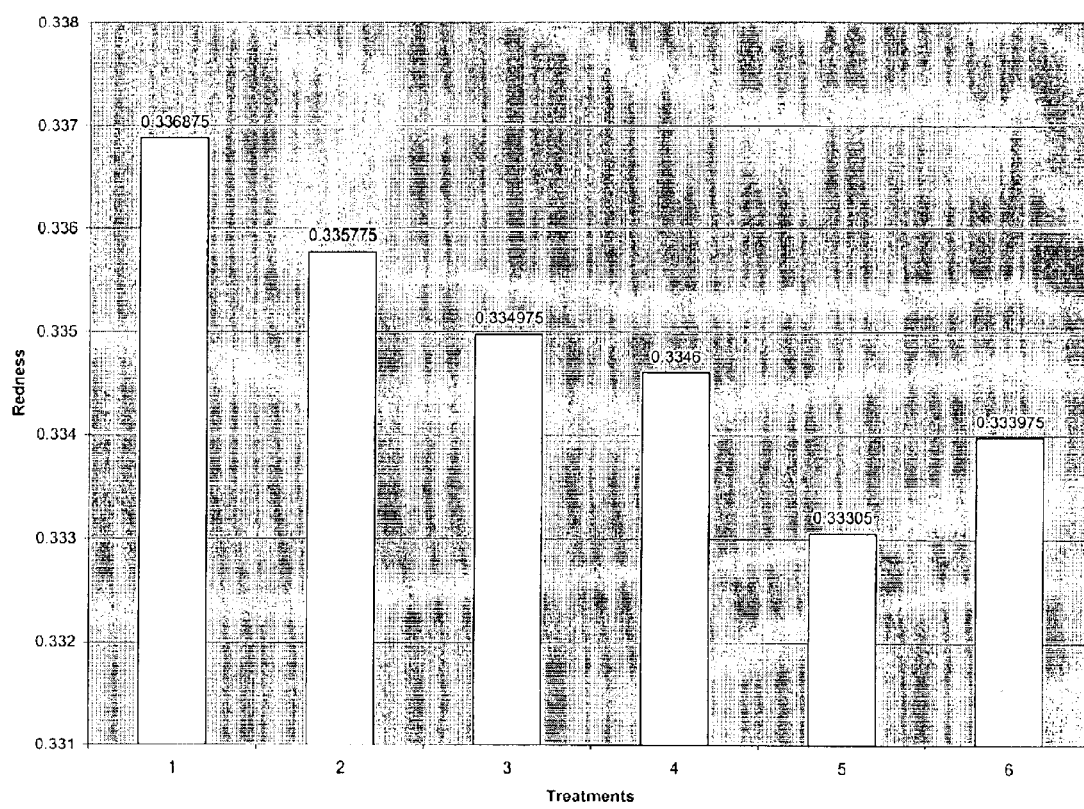
FIG. 7. Decrease in the redness color of red wheat after treating the seeds with hypochlorite. Treatments are: 1=Dry seeds (red wheat control); 2=Water steep; 3=Hypochlorite 0.8%; 4=Hypochlorite 0.8%+NaOH; 5=Hypochlorite 1.6%; 6=Hypochlorite 1.6%+NaOH. The time used was 1 hour and the sodium hydroxide concentration was 0.25%.

Table 9 shows an increase in the lightness of the flower of seeds that were submitted to the hypochlorite solutions as well as a reduction in the redness. The lightness values increased from 63.9 to 71.0 for *Triticum durum* and from 64.8 to 72.8 for *Triticum aestivum*. The reduction in redness was more pronounced in the red wheat (*T. aestivum*) with values from 0.3336 in the control treatment to 0.3330 in the 1.6% hypochlorite solution. Hypochlorite treatments also tended to reduce the percentage of both aleurone and pericarp layers (Table 9). This effect of color improvement might be associated with the reactions that take place at the surface of the seeds, where most of the color pigments are present. An illustration of part of the *Triticum aestivum* data above is shown in FIGS. 6 and 7.

TABLE 10

Effect of chemical treatments on seed color values on red wheat. Variety used: Vance Wheat (red), lot # JR9276-A.

| Treatments | Color values* | |
| --- | --- | --- |
| | Lightness | Aleurone (%) Redness |
| 1. Dry seeds (red wheat control) | 64.805 | 0.335575 |
| 2. Water steep (0.5 h) – control | 64.68 | 0.335875 |
| 3. Hypochlorite 0.8% (0.5 h) | 70.5025 | 0.33465 |
| 4. Hypochlorite 1.6% (0.5 h) | 71.8475 | 0.332675 |
| 5. Hypochlorite 3.3% (0.5 h) | 72.7825 | 0.333175 |
| 6. NaOH 0.25% (0.5 h) | 63.6275 | 0.33615 |
| 7. NaOH 0.25% + Hypochlorite 0.8% (0.5 h) | 69.955 | 0.3344 |
| 8. NaOH 0.25% + Hypochlorite 1.6% (0.5 h) | 71.5875 | 0.33295 |
| 9. NaOH 0.25% + Hypochlorite 3.3% (0.5 h) | 73.4725 | 0.3325 |
| 10. Water steep (1 h) – control | 65.6875 | 0.335925 |
| 11. Hypochlorite 0.8% (1 h) | 73.0425 | 0.333475 |
| 12. Hypochlorite 1.6% (1 h) | 74.1725 | 0.332125 |
| 13. Hypochlorite 3.3% (1 h) | 75.8925 | 0.33155 |
| 14. NaOH 0.25% (1 h) | 65.26 | 0.3371 |
| 15. NaOH 0.25% + Hypochlorite 0.8% (1 h) | 71.2625 | 0.33355 |
| 16. NaOH 0.25% + Hypochlorite 1.6% (1 h) | 72.9125 | 0.3321 |
| 17. NaOH 0.25% + Hypochlorite 3.3% (1 h) | 74.03 | 0.3327 |
| 18. Water steep (2 h) – control | 66.8175 | 0.33545 |
| 19. Hypochlorite 0.8% (2 h) | 73.68 | 0.331775 |
| 20. Hypochlorite 1.6% (2 h) | 75.675 | 0.331375 |
| 21. Hypochlorite 3.3% (2 h) | 76.85 | 0.33115 |
| 22. NaOH 0.25% (2 h) | 64.1125 | 0.337775 |
| 23. NaOH 0.25% + Hypochlorite 0.8% (2 h) | 72.94 | 0.331975 |
| 24. NaOH 0.25% + Hypochlorite 1.6% (2 h) | 74.5175 | 0.33165 |
| 25. NaOH 0.25% + Hypochlorite 3.3% (2 h) | 75.535 | 0.331275 |
| 26. White wheat control | 79.2525 | 0.331675 |

*Color values were obtained using a Minolta C100 Chroma Meter. Numerical values were expressed in the "Yxy" color system where Y relates to "lightness", in percent and x indicates reduced red color. Numbers are means of four replications.

Figure 8:
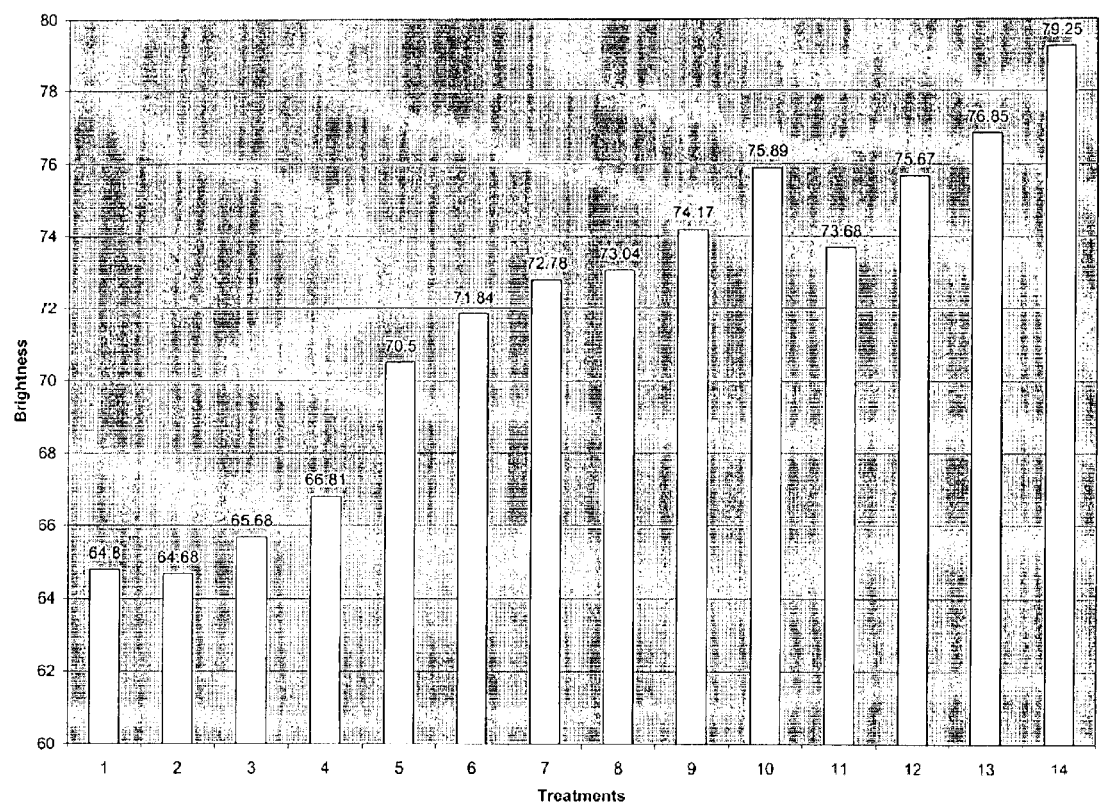
FIG. 8. Increase in the lightness color of red wheat after treating the seeds with hypochlorite. Treatments are: 1=Dry seeds (red wheat control); 2, 3 and 4=Water steep for 0.5, 1 and 2 hours; 5, 6 and 7=Hypochlorite at 0.8, 1.6 and 3.3% for 0.5 h; 8, 9 and 10=Hypochlorite at 0.8, 1.6 and 3.3% for 1 h; 11,12 and 13=Hypochlorite at 0.8, 1.6 and 3.3% for 2 h; 14=dry seeds of white wheat (control).
Figure 9:
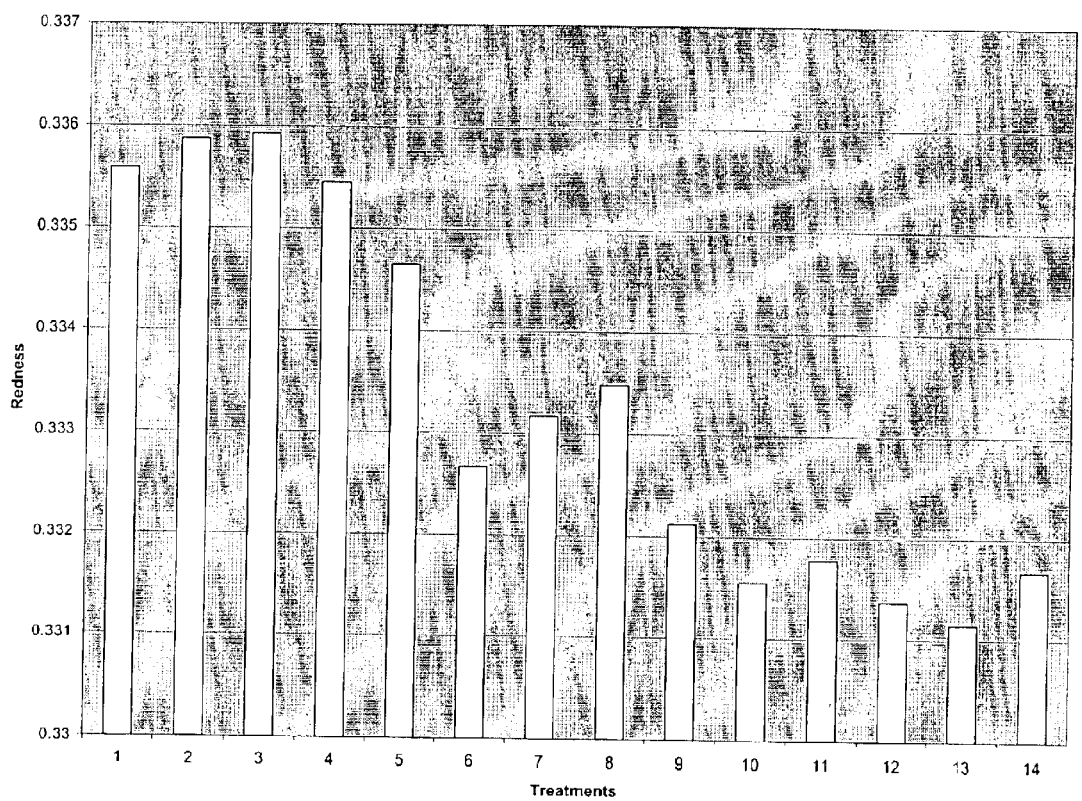
FIG. 9. Reduction in the value of redness color of red wheat after treating the seeds with hypochlorite. Treatments are: 1=Dry seeds (red wheat control); 2, 3 and 4=Water steep for 0.5, 1 and 2 hours; 5, 6 and 7=Hypochlorite at 0.8, 1.6 and 3.3% for 0.5 h; 8, 9 and 10=Hypochlorite at 0.8, 1.6 and 3.3% for 1 h; 11,12 and 13=Hypochlorite at 0.8, 1.6 and 3.3% for 2 h; 14=dry seeds of white wheat (control).

The data from Table 10 shows a significant increment in lightness and reduction in redness of red wheat submitted to the hypochlorite solution. The effects are more pronounced as time increases (from 0.5 hour to 2 hours) and as the concentration increases (from 0.8 to 3.3%). The addition of sodium hydroxide tends to reduce the effect of hypochlorite. Treating red seeds with hypochlorite for two hours increased the lightness of the red wheat from 64.8 to 76.8 and reduced the redness of the flower from 0.3355 to 0.3311. This improvement in color is remarkable, almost reaching the values for white wheat in lightness (79.2) and reducing further its value in redness (0.3316). An illustration from some of the treatments above is shown in FIGS. 8 and 9.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. A method of treating a grain or seed to reduce the contamination level of seed-associated pathogenic fungi, or a toxin from a seed associated pathogenic fungi, comprising contacting the grain or seed with a treatment solution consisting essentially of hypochlorite at a concentration of about 0.1% to about 12% v/v at a starting pH of above about 5.0 and an additional chemical for a period of time, wherein the fungus is *Fusarium graminearum, Fusarium solani* or other *Fusarium* spp., *Bipolaris sorokiniona, Dreclaslera teres, Drechslera tritici-repentis, Drechslera avenae* or other *Drechslera* spp., *Helminthosporium* spp, *Alternaria* spp., *Diplodia* spp., *Septoria tritici* or other *Septona* spp., or *Stagonospora nodoru*, wherein the toxin contamination is by Deoxynivalenol (DON), Nivalenol, Zearalenone, Trichothecenes, Moniliforniin, Fumonisins, Ochratoxin A, Citrinin, or Patulin, and wherein the additional chemical is sodium hydroxide, potassium hydroxide, sodium phosphate dibasic, sodium bicarbonate, glacial acetic acid or peracetic acid.

2. The method of claim 1, wherein the hypochlorite is at a concentration of about 0.5 to about 3.3% v/v.

3. The method of claim 1, wherein the hypochlorite is at a concentration of about 0.8 to about 1.2% v/v.

4. The method of claim 1, wherein the pH is above about 13.0.

5. The method of claim 1, wherein the period of time is for at least 1 second.

6. The method of claim 5, wherein the time period is from about 5 minutes to about 30 minutes.

7. The method of claim 1, wherein the contacting step takes place at a temperature of about 40 to 150° F.

8. The method of claim 1, wherein the contacting step takes place at a temperature of about 60 to 80° F.

9. The method of claim 1, wherein the contamination level is reduced by 0.1% to 100%.

10. The method of claim 1, wherein the contamination level is reduced by 80% to 90%.

11. The method of claim 1, wherein the contamination is caused by a fungus.

12. The method of claim 11, wherein the fungus is *Fusarium graminearum, Fusarium solani* or other *Fusarium* spp., *Bipolaris sorokiniana, Drechslera teres, Drechslera tritici-repentis, Drechslera avenae* or other *Drechslera* spp., *Helminthosporium* spp., *Allernaria* spp., *Daplodla* spp., *Septoria tritict* or other *Septaria* spp., or *Stagonospora nodorum.*

13. The method of claim 1, wherein the toxin contamination is by Deoxynivalenol (DON), Nivalenol, Zearalenone, Trichothecenes, Moniliformin, Fumonisins, Ochratoxm A, Citrinin, or Patulin.

14. The method of claim 1, wherein the toxin contamination is by Deoxynivalenol (DON), Nivalenol, or Zearalenone.

15. The method of claim 1, wherein the grain or seed is a wheat, barley, corn, soybean, oats, rice, rye, sorghum, peanut, canola, clover, pasture seed, cucurbit seed, flower seed, or vegetable seed.

16. The method of claim 1, wherein the grain or seed is a wheat, barley, corn, soybean, or oats.

17. The method of claim 1, wherein the method increases germination rates of the grain or seed.

18. A method of treating a grain or seed to reduce the contamination level of a toxin from a seed associated pathogenic fungi, comprising contacting the grain or seed with a treatment solution comprising hypochlorite at a concentration of about 0.1% to about 12% v/v at a starting pH of above about 5.0 for a period of time, wherein the toxin contamination is by Deoxynivalenol (DON), Nivaleno, *Zearalenone, Trichothecenes, Moniliformin, Fumonisins, Ochratoxin A, Citrinin, or Patulin.*

19. The method of claim 18, wherein the hypochlorite is at a concentration of about 0.5 to about 3.3% v/v.

20. The method of claim 18, wherein the hypochlorite is at a concentration of about 0.8 to about 1.2% v/v.

21. The method of claim 18, wherein the pH is above about 13.0.

22. The method of claim 18, wherein the period of time is for at least 1 second.

23. The method of claim 22, wherein the time period is from about 5 minutes to about 30 minutes.

24. The method of claim 18, wherein the contacting step takes place at a temperature of about 40 to 150° F.

25. The method of claim 18, wherein the contacting step takes place at a temperature of about 60 to 80° F.

26. The method of claim 18, wherein the contamination level is reduced by 0.1% to 100%.

27. The method of claim 18, wherein the contamination level is reduced by 80% to 90%.

28. The method of claim 18, further comprising an additional chemical.

29. The method of claim 28, wherein the additional chemical is an alkali buffer or acid.

30. The method of claim 18, wherein the additional chemical is sodium hydroxide, potassium hydroxide, sodium phosphate dibasic, sodium bicarbonate, glacial acetic acid or peracetic acid.

31. The method of claim 18, wherein the toxin contamination is by Deoxynivalenol (DON), Nivalenol, or Zearalenone.

32. The method of claim 18, wherein the grain or seed is a wheat, barley, corn, soybean, oats, rice, rye, sorghum, peanut, canola, clover, pasture seed, cucurbit seed, flower seed, or vegetable seed.

33. The method of claim 18, wherein the grain or seed is a wheat, barley, corn, soybean, or oats.

34. The method of claim 18, wherein the method increases germination rates of the grain or seed.

* * * * *

UNITED STATES PATENT AND TRADEMARK OFFICE
CERTIFICATE OF CORRECTION

PATENT NO. : 6,927,192 B2
APPLICATION NO. : 10/367604
DATED : August 9, 2005
INVENTOR(S) : Jose A. Martinelli, Marcia Martinelli and R. Gary Fulcher It is certified that error appears in the above-identified patent and that said Letters Patent is hereby corrected as shown below:

In column 16, line 57, claim 1, delete "*sorokiniona*" and insert --*sorokiniana*--, therefor.

In column 16, line 57, claim 1, delete "*Dreclaslera*" and insert --*Drechslera*--, therefor.

In column 16, line 60, claim 1, delete "*Septona*" and insert --*Septoria*--, therefor.

In column 16, line 63, claim 1, delete "Moniliforniin" and insert --Moniliformin--, therefor.

In column 17, line 25, claim 12, delete "*Allernaria*" and insert --*Alternaria*--, therefor.

In column 17, line 25, claim 12, delete "*Daplodla*" and insert --*Diplodia*--, therefor.

In column 17, line 26, claim 12, delete "*tritici*" and insert --*tritici*--, therefor.

In column 17, line 26, claim 12, delete "*Septaria*" and insert --*Septoria*--, therefor.

In column 17, line 31, claim 13, delete "Ochratoxm" and insert --Ochratoxin--, therefor.

In column 18, line 4, claim 18, delete "Nivaleno" and insert --Nivalenol--, therefor.

In column 18, line 5, claim 18, delete "*Zearalenone, Trichothecenes, Moniliformin, Fumonisins,*" and insert -- Zearalenone, Trichothecenes, Moniliformin, Fumonisins,--, therefor.

UNITED STATES PATENT AND TRADEMARK OFFICE
CERTIFICATE OF CORRECTION

PATENT NO. : 6,927,192 B2
APPLICATION NO. : 10/367604
DATED : August 9, 2005
INVENTOR(S) : Jose A. Martinelli, Marcia Martinelli and R. Gary Fulcher It is certified that error appears in the above-identified patent and that said Letters Patent is hereby corrected as shown below:

In column 18, line 6, claim 18, delete "*Ochratoxin A, Citrinin, or Patulin*" and insert --Ochratoxin A, Citrinin, or Patulin--, therefor.

Signed and Sealed this

Twenty-second Day of May, 2007

JON W. DUDAS
*Director of the United States Patent and Trademark Office*